US011577085B2

(12) United States Patent
Koop et al.

(10) Patent No.: US 11,577,085 B2
(45) Date of Patent: Feb. 14, 2023

(54) DELIVERY DEVICES AND METHODS FOR LEADLESS CARDIAC DEVICES

(71) Applicant: CARDIAC PACEMAKERS, INC., St. Paul, MN (US)

(72) Inventors: Brendan Early Koop, Ham Lake, MN (US); Benjamin J. Haasl, Forest Lake, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 701 days.

(21) Appl. No.: 16/052,829

(22) Filed: Aug. 2, 2018

(65) Prior Publication Data

US 2019/0038906 A1    Feb. 7, 2019

Related U.S. Application Data

(60) Provisional application No. 62/540,646, filed on Aug. 3, 2017.

(51) Int. Cl.
*A61N 1/375* (2006.01)
*A61N 1/372* (2006.01)
*A61N 1/05* (2006.01)

(52) U.S. Cl.
CPC ....... *A61N 1/37512* (2017.08); *A61N 1/3756* (2013.01); *A61N 1/37205* (2013.01); *A61N 1/059* (2013.01)

(58) Field of Classification Search
CPC ............ A61N 1/37512; A61N 1/37205; A61N 1/3756; A61N 1/059; A61B 1/00135; A61B 1/00154

USPC .......................................................... 607/122
See application file for complete search history.

(56) References Cited

U.S. PATENT DOCUMENTS

| 4,301,815 A | 11/1981 | Doring |
| 5,807,399 A | 9/1998 | Laske et al. |
| 5,908,381 A | 6/1999 | Aznoian et al. |
| 6,181,973 B1 | 1/2001 | Ceron et al. |

(Continued)

FOREIGN PATENT DOCUMENTS

| EP | 2818201 B1 | 7/2016 |
| EP | 2658599 B1 | 10/2016 |

(Continued)

*Primary Examiner* — Gary Jackson
*Assistant Examiner* — Alexander M Eisenberg
(74) *Attorney, Agent, or Firm* — Seager, Tufte & Wickhem LLP

(57) ABSTRACT

Delivery devices, systems, and methods for delivering implantable leadless pacing devices are disclosed. An example delivery device may include an outer tubular member including a lumen extending from a proximal end to a distal end thereof and an intermediate tubular member including a lumen extending from a proximal end to a distal end thereof. A distal holding section may be coupled to the intermediate tubular member and define a cavity therein for receiving a proximal implantable leadless pacing device and a distal implantable leadless pacing device in a linear arrangement. The distal holding section may have a proximal body portion and a distal body portion. The proximal body portion may be more flexible than the distal body portion. An inner tubular member including a lumen extending from a proximal end to a distal end thereof may be slidably disposed within the lumen of the intermediate tubular member.

20 Claims, 16 Drawing Sheets

(56) References Cited

U.S. PATENT DOCUMENTS

| | | |
|---|---|---|
| 6,224,725 B1 | 5/2001 | Glocker |
| 6,395,017 B1 | 5/2002 | Dwyer et al. |
| 6,409,674 B1 | 6/2002 | Brockway et al. |
| 6,497,803 B2 | 12/2002 | Glocker et al. |
| 6,551,477 B2 | 4/2003 | Glocker et al. |
| 6,582,441 B1 | 6/2003 | He et al. |
| 6,638,268 B2 | 10/2003 | Niazi |
| 6,786,918 B1 | 9/2004 | Krivoruchko et al. |
| 7,248,913 B2 | 7/2007 | Hassett |
| 7,321,798 B2 | 1/2008 | Muhlenberg et al. |
| 7,381,216 B2 | 6/2008 | Buzzard et al. |
| 7,499,758 B2 | 3/2009 | Cates et al. |
| 7,509,169 B2 | 3/2009 | Eigler et al. |
| 7,608,099 B2 | 10/2009 | Johnson et al. |
| 7,666,203 B2 | 2/2010 | Chanduszko et al. |
| 7,678,081 B2 | 3/2010 | Whiting et al. |
| 7,799,037 B1 | 9/2010 | He et al. |
| 7,840,281 B2 | 11/2010 | Kveen et al. |
| 7,937,161 B2 | 5/2011 | Hastings et al. |
| 7,993,351 B2 | 8/2011 | Worley et al. |
| 8,002,822 B2 | 8/2011 | Glocker et al. |
| 8,010,209 B2 | 8/2011 | Jacobson |
| 8,103,361 B2 | 1/2012 | Moser |
| 8,185,213 B2 | 5/2012 | Kveen et al. |
| 8,267,987 B2 | 9/2012 | Johnson et al. |
| 8,352,028 B2 | 1/2013 | Wenger |
| 8,364,280 B2 | 1/2013 | Marnfeldt et al. |
| 8,382,813 B2 | 2/2013 | Shumer |
| 8,428,750 B2 | 4/2013 | Kolberg |
| 8,478,431 B2 | 7/2013 | Griswold et al. |
| 8,504,156 B2 | 8/2013 | Bonner et al. |
| 8,527,068 B2 | 9/2013 | Ostroff |
| 8,532,790 B2 | 9/2013 | Griswold |
| 8,548,605 B2 | 10/2013 | Ollivier |
| 8,615,310 B2 | 12/2013 | Khairkhahan et al. |
| 8,634,912 B2 | 1/2014 | Bornzin et al. |
| 8,721,587 B2 | 5/2014 | Berthiaume et al. |
| 8,727,996 B2 | 5/2014 | Allan et al. |
| 8,758,365 B2 | 6/2014 | Bonner et al. |
| 8,855,789 B2 | 10/2014 | Jacobson |
| 8,894,824 B2 | 11/2014 | Glocker et al. |
| 8,903,513 B2 | 12/2014 | Ollivier |
| 8,926,588 B2 | 1/2015 | Berthiaume et al. |
| 8,945,145 B2 | 2/2015 | Tran et al. |
| 8,945,146 B2 | 2/2015 | Steingisser et al. |
| 8,948,883 B2 | 2/2015 | Eggen et al. |
| 8,958,892 B2 | 2/2015 | Khairkhahan et al. |
| 9,020,611 B2 | 4/2015 | Khairkhahan et al. |
| 9,072,872 B2 | 7/2015 | Asleson et al. |
| 9,101,281 B2 | 8/2015 | Reinert et al. |
| 9,119,959 B2 | 9/2015 | Rys et al. |
| 9,126,032 B2 | 9/2015 | Khairkhahan et al. |
| 9,155,479 B2 | 10/2015 | Solem |
| 9,155,882 B2 | 10/2015 | Grubac et al. |
| 9,168,372 B2 | 10/2015 | Fain |
| 9,204,842 B2 | 12/2015 | Mothilal et al. |
| 9,205,225 B2 | 12/2015 | Khairkhahan et al. |
| 9,216,293 B2 | 12/2015 | Berthiaume et al. |
| 9,220,906 B2 | 12/2015 | Griswold et al. |
| 9,238,145 B2 | 1/2016 | Wenzel et al. |
| 9,242,102 B2 | 1/2016 | Khairkhahan et al. |
| 9,272,155 B2 | 3/2016 | Ostroff |
| 9,283,381 B2 | 3/2016 | Grubac et al. |
| 9,283,382 B2 | 3/2016 | Berthiaume et al. |
| 9,283,392 B2 | 3/2016 | Moore et al. |
| 9,308,365 B2 | 4/2016 | Nordstrom et al. |
| 9,308,374 B2 | 4/2016 | Kveen et al. |
| 9,339,197 B2 | 5/2016 | Griswold et al. |
| 9,351,648 B2 | 5/2016 | Mothilal et al. |
| 9,358,387 B2 | 6/2016 | Suwito et al. |
| 9,414,857 B2 | 8/2016 | Wood et al. |
| 9,421,384 B2 | 8/2016 | Taff et al. |
| 9,433,780 B2 | 9/2016 | Regnier et al. |
| 9,446,248 B2 | 9/2016 | Sheldon et al. |
| 9,463,315 B2 | 10/2016 | Bornzin et al. |
| 9,468,773 B1 | 10/2016 | Anderson et al. |
| 9,504,820 B2 | 11/2016 | Bonner et al. |
| 9,511,236 B2 | 12/2016 | Varady et al. |
| 9,517,336 B2 | 12/2016 | Eggen et al. |
| 9,517,337 B2 | 12/2016 | Ollivier |
| 9,526,522 B2 | 12/2016 | Wood et al. |
| 9,526,891 B2 | 12/2016 | Eggen et al. |
| 9,539,423 B2 | 1/2017 | Bonner et al. |
| 9,555,236 B2 | 1/2017 | Regnier et al. |
| 9,579,500 B2 | 2/2017 | Rys et al. |
| 9,597,514 B2 | 3/2017 | Khairkhahan et al. |
| 9,610,454 B2 | 4/2017 | Doan et al. |
| 9,623,234 B2 | 4/2017 | Anderson |
| 9,662,487 B2 | 5/2017 | Kveen et al. |
| 9,675,798 B2 | 6/2017 | Grubac et al. |
| 9,717,421 B2 | 8/2017 | Griswold et al. |
| 9,724,507 B2 | 8/2017 | Wood et al. |
| 9,750,931 B2 | 9/2017 | Wood et al. |
| 9,764,139 B2 | 9/2017 | Christensen |
| 9,775,982 B2 | 10/2017 | Grubac et al. |
| 9,808,617 B2 | 11/2017 | Ostroff et al. |
| 9,808,629 B2 | 11/2017 | Steingisser et al. |
| 9,814,896 B2 | 11/2017 | Solem |
| 9,833,625 B2 | 12/2017 | Waldhauser et al. |
| 9,833,626 B2 | 12/2017 | Klimovitch et al. |
| 9,844,659 B2 | 12/2017 | Grubac et al. |
| 9,844,664 B2 | 12/2017 | McEvoy et al. |
| 9,861,815 B2 | 1/2018 | Tran et al. |
| 9,867,982 B2 | 1/2018 | Berthiaume et al. |
| 2003/0078618 A1 | 4/2003 | Fey et al. |
| 2005/0101984 A1 | 5/2005 | Chanduszko et al. |
| 2005/0119525 A1* | 6/2005 | Takemoto .......... A61B 1/00154 600/114 |
| 2005/0165472 A1 | 7/2005 | Glocker |
| 2005/0209653 A1 | 9/2005 | Herbert et al. |
| 2005/0267555 A1 | 12/2005 | Marnfeldt et al. |
| 2006/0009737 A1 | 1/2006 | Whiting et al. |
| 2006/0293559 A1* | 12/2006 | Grice, III .......... A61B 1/00135 600/102 |
| 2009/0082828 A1 | 3/2009 | Ostroff |
| 2009/0171408 A1 | 7/2009 | Solem |
| 2010/0274227 A1 | 10/2010 | Khairkhahan et al. |
| 2011/0112548 A1 | 5/2011 | Fifer et al. |
| 2011/0270339 A1 | 11/2011 | Murray, III et al. |
| 2011/0270340 A1 | 11/2011 | Pellegrini et al. |
| 2012/0095539 A1 | 4/2012 | Khairkhahan et al. |
| 2012/0109148 A1 | 5/2012 | Bonner et al. |
| 2012/0158111 A1* | 6/2012 | Khairkhahan ..... A61N 1/37205 607/127 |
| 2012/0172690 A1 | 7/2012 | Anderson et al. |
| 2012/0172891 A1 | 7/2012 | Lee |
| 2012/0172892 A1* | 7/2012 | Grubac ................ A61N 1/0573 606/129 |
| 2013/0012925 A1 | 1/2013 | Berthiaume et al. |
| 2013/0035636 A1 | 2/2013 | Beasley et al. |
| 2013/0103047 A1 | 4/2013 | Steingisser et al. |
| 2013/0253342 A1 | 9/2013 | Griswold et al. |
| 2013/0253346 A1 | 9/2013 | Griswold et al. |
| 2014/0018818 A1 | 1/2014 | Somogyi et al. |
| 2014/0324145 A1 | 10/2014 | Eggen et al. |
| 2014/0378991 A1 | 12/2014 | Ollivier |
| 2014/0379048 A1* | 12/2014 | Von Arx ............. A61N 1/37288 607/60 |
| 2015/0039070 A1 | 2/2015 | Kuhn et al. |
| 2015/0045868 A1 | 2/2015 | Bonner et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1* | 2/2015 | Schmidt ............. A61N 1/37205 607/127 |
| 2015/0094668 A1 | 4/2015 | Wood et al. |
| 2015/0094735 A1 | 4/2015 | Ward et al. |
| 2015/0283376 A1 | 10/2015 | Ollivier et al. |
| 2015/0306378 A1 | 10/2015 | Schmidt et al. |
| 2015/0306381 A1 | 10/2015 | Schmidt et al. |

(56) References Cited

U.S. PATENT DOCUMENTS

| | | |
|---|---|---|
| 2015/0335884 A1 | 11/2015 | Khairkhahan et al. |
| 2015/0352351 A1* | 12/2015 | Muessig ............... A61N 1/3756 606/129 |
| 2016/0000563 A1 | 1/2016 | Asleson et al. |
| 2016/0007924 A1 | 1/2016 | Eigler et al. |
| 2016/0015287 A1 | 1/2016 | Anderson et al. |
| 2016/0015322 A1 | 1/2016 | Anderson et al. |
| 2016/0051826 A1 | 2/2016 | Solem |
| 2016/0059003 A1 | 3/2016 | Eggen et al. |
| 2016/0067446 A1 | 3/2016 | Klenk et al. |
| 2016/0067447 A1 | 3/2016 | Paspa et al. |
| 2016/0067503 A1 | 3/2016 | Berthiaume et al. |
| 2016/0082270 A1 | 3/2016 | Mothilal et al. |
| 2016/0096001 A1* | 4/2016 | Eidenschink ....... A61M 25/008 606/129 |
| 2016/0114156 A1* | 4/2016 | Haasl ................. A61N 1/0587 606/129 |
| 2016/0114157 A1 | 4/2016 | Haasl et al. |
| 2016/0121129 A1* | 5/2016 | Persson ................ A61N 1/3756 607/32 |
| 2016/0158560 A1 | 6/2016 | Moore et al. |
| 2016/0206872 A1 | 7/2016 | Wood et al. |
| 2016/0213919 A1 | 7/2016 | Suwito et al. |
| 2016/0220829 A1 | 8/2016 | Wood |
| 2016/0228715 A9 | 8/2016 | Bonner et al. |
| 2016/0235971 A1 | 8/2016 | Wood et al. |
| 2016/0243350 A9 | 8/2016 | Grubac et al. |
| 2016/0243355 A1 | 8/2016 | Wood |
| 2016/0263372 A1 | 9/2016 | Wood et al. |
| 2016/0271388 A1 | 9/2016 | Ollivier et al. |
| 2016/0279423 A1 | 9/2016 | Kelly et al. |
| 2016/0296761 A1 | 10/2016 | Doan et al. |
| 2016/0310703 A1 | 10/2016 | Drake et al. |
| 2016/0310722 A1* | 10/2016 | Demmer ................. A61N 1/059 |
| 2016/0310723 A1 | 10/2016 | Eggen et al. |
| 2016/0310726 A1 | 10/2016 | Demmer et al. |
| 2016/0310747 A1 | 10/2016 | Grubac et al. |
| 2016/0325104 A1 | 11/2016 | Anderson et al. |
| 2016/0361536 A1 | 12/2016 | Grubac et al. |
| 2017/0028190 A1 | 2/2017 | O'Carroll et al. |
| 2017/0028194 A1 | 2/2017 | Bonner et al. |
| 2017/0043158 A1 | 2/2017 | Kelly et al. |
| 2017/0065369 A1 | 3/2017 | Bornzin et al. |
| 2017/0072191 A1 | 3/2017 | Ma et al. |
| 2017/0095662 A1 | 4/2017 | McDonnell et al. |
| 2017/0100582 A1 | 4/2017 | McEvoy et al. |
| 2017/0106185 A1 | 4/2017 | Orts et al. |
| 2017/0113035 A1 | 4/2017 | Bonner et al. |
| 2017/0119999 A1 | 5/2017 | Kelly |
| 2017/0136231 A1 | 5/2017 | Kelly et al. |
| 2017/0143955 A1 | 5/2017 | Soltis et al. |
| 2017/0143980 A1 | 5/2017 | Soltis et al. |
| 2017/0151429 A1 | 6/2017 | Regnier |
| 2017/0165479 A1 | 6/2017 | Rys et al. |
| 2017/0189681 A1 | 7/2017 | Anderson |
| 2017/0209688 A1 | 7/2017 | Drake et al. |
| 2017/0209689 A1 | 7/2017 | Chen et al. |
| 2017/0209690 A1 | 7/2017 | Drake et al. |
| 2017/0216575 A1 | 8/2017 | Asleson et al. |
| 2017/0224997 A1 | 8/2017 | Shuros et al. |
| 2017/0274202 A1 | 9/2017 | Grubac et al. |
| 2017/0304624 A1 | 10/2017 | Friedman et al. |
| 2017/0312479 A1 | 11/2017 | Keaveney et al. |
| 2017/0312496 A1 | 11/2017 | Wood et al. |
| 2017/0319847 A1 | 11/2017 | Ho et al. |
| 2017/0326369 A1 | 11/2017 | Koop et al. |
| 2017/0326372 A1 | 11/2017 | Koop et al. |
| 2017/0326373 A1 | 11/2017 | Delanely, Jr. et al. |
| 2017/0340316 A1 | 11/2017 | Wood et al. |
| 2017/0340877 A1 | 11/2017 | Ollivier |
| 2017/0368338 A1 | 12/2017 | Madden et al. |

FOREIGN PATENT DOCUMENTS

| | | | |
|---|---|---|---|
| EP | 1968698 B1 | 11/2016 | |
| EP | 2651502 B1 | 11/2016 | |
| EP | 2771064 B1 | 1/2017 | |
| EP | 2780077 B1 | 1/2017 | |
| WO | 2007068284 A1 | 6/2007 | |
| WO | WO 2016/191754 A1 * | 12/2016 | ............ A61M 29/02 |

* cited by examiner

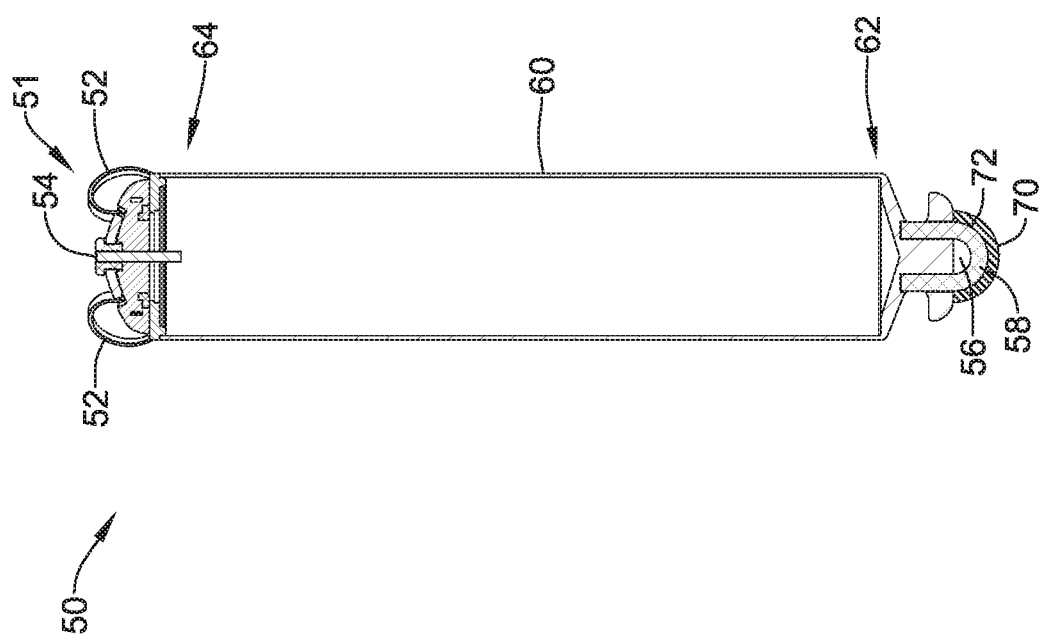

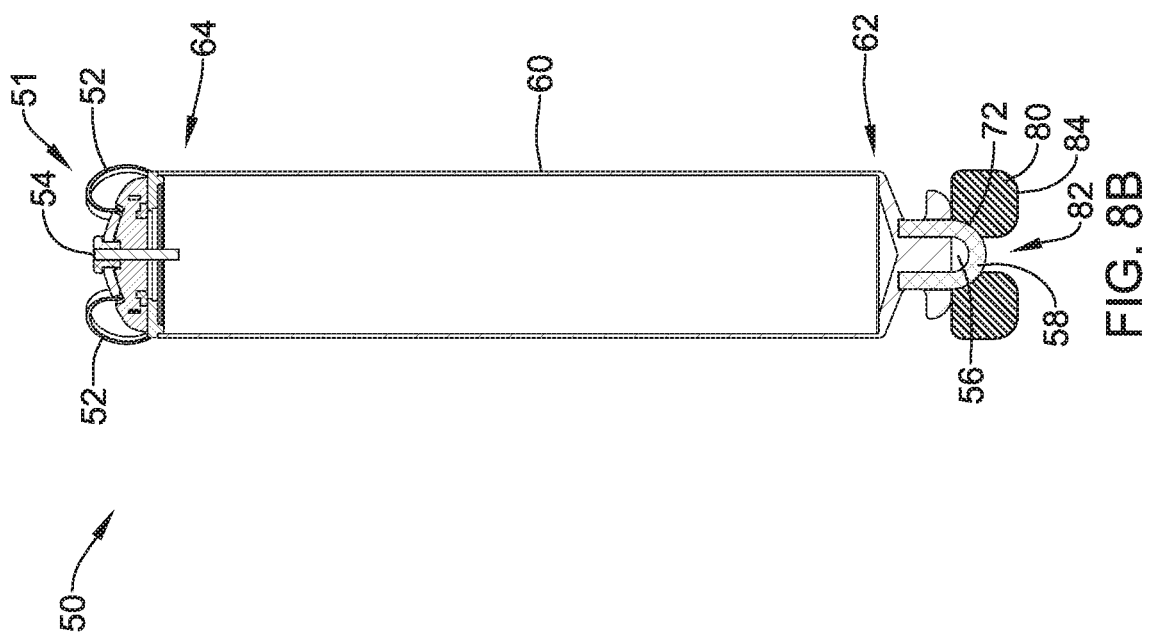

DELIVERY DEVICES AND METHODS FOR LEADLESS CARDIAC DEVICES

CROSS REFERENCE TO RELATED APPLICATIONS

The present application claims the benefit of and priority to U.S. Provisional Patent Application No. 62/540,646, filed Aug. 3, 2017, the disclosure of which is incorporated herein by reference.

TECHNICAL FIELD

The present disclosure pertains to medical devices, and methods for manufacturing and/or using medical devices. More particularly, the present disclosure pertains to leadless cardiac devices and methods, such as leadless pacing devices and methods, and delivery devices and methods for such leadless devices.

BACKGROUND

A wide variety of medical devices have been developed for medical use, for example, cardiac use. Some of these devices include catheters, leads, pacemakers, and the like, and delivery devices and/or systems used for delivering such devices. These devices are manufactured by any one of a variety of different manufacturing methods and may be used according to any one of a variety of methods. Of the known medical devices, delivery systems, and methods, each has certain advantages and disadvantages. There is an ongoing need to provide alternative medical devices and delivery devices as well as alternative methods for manufacturing and using medical devices and delivery devices.

BRIEF SUMMARY

This disclosure provides design, material, manufacturing method, and use alternatives for medical devices, including delivery devices.

In a first example, a delivery device for delivering two or more implantable leadless pacing devices may comprise a tubular member including a lumen extending from a proximal end to a distal end thereof, a distal holding section located at the distal end of the tubular member and defining a cavity therein, the distal holding section having a proximal body portion and a distal body portion and a first implantable leadless pacing device and a second implantable leadless pacing device positioned within the distal holding section in a linear arrangement.

Alternatively or additionally to any of the examples above, in another example, the proximal body portion may be more flexible than the distal body portion.

Alternatively or additionally to any of the examples above, in another example, the proximal body portion and the distal body portion may comprise different materials.

Alternatively or additionally to any of the examples above, in another example, the proximal body portion may be configured to move between a first expanded configuration and a second collapsed configuration.

Alternatively or additionally to any of the examples above, in another example, when at least one of the first or second implantable leadless pacing devices are positioned adjacent to the proximal body portion, the proximal body portion may be held in the expanded configuration.

Alternatively or additionally to any of the examples above, in another example, distal actuation of the first or second implantable leadless device may cause at least a portion of the proximal body portion to move from the expanded configuration to the collapsed configuration.

Alternatively or additionally to any of the examples above, in another example, the distal body portion may further comprise a reinforcing element.

Alternatively or additionally to any of the examples above, in another example, the first implantable leadless pacing device may be positioned proximal to the second implantable leadless pacing device.

Alternatively or additionally to any of the examples above, in another example, a proximal end of the second implantable leadless pacing device may be nested within a distal end region of the first implantable leadless pacing device.

Alternatively or additionally to any of the examples above, in another example, the second implantable leadless pacing device may have a smaller cross-sectional area than the first implantable leadless pacing device.

Alternatively or additionally to any of the examples above, in another example, the second implantable leadless pacing device may have a similar cross-sectional area to the first implantable leadless pacing device.

Alternatively or additionally to any of the examples above, in another example, the delivery device may further comprise an atraumatic element positioned on a proximal end of the second implantable leadless pacing device.

Alternatively or additionally to any of the examples above, in another example, the atraumatic element may comprise a silicone bumper.

Alternatively or additionally to any of the examples above, in another example, the atraumatic element may comprise a bioabsorbable ring.

Alternatively or additionally to any of the examples above, in another example, the proximal body portion may have a length similar to a length of a more distal of the first or second implantable leadless pacing devices and the distal body portion may have a length similar to a length of a more proximal of the first or second implantable leadless pacing devices.

In another example, a delivery device for delivering two or more implantable leadless pacing devices may comprise a tubular member including a lumen extending from a proximal end to a distal end thereof, a distal holding section located at the distal end of the tubular member and defining a cavity therein for receiving a proximal implantable leadless pacing device and a distal implantable leadless pacing device in a linear arrangement. The distal holding section has a proximal body portion comprising a first material and a distal body portion comprising a second material different from the first material. An inner member is slidably disposed within the lumen of the tubular member. The inner member is configured to be longitudinally actuated relative to the tubular member to deploy the proximal implantable leadless pacing device and the distal implantable leadless pacing device from the distal holding section. The proximal body portion is configured to move between a first expanded configuration and a second collapsed configuration upon deployment of the distal implantable leadless pacing device.

Alternatively or additionally to any of the examples above, in another example, the proximal body portion may be more flexible than the distal body portion.

Alternatively or additionally to any of the examples above, in another example, the proximal body portion and the distal body portion may comprise different materials.

Alternatively or additionally to any of the examples above, in another example, the proximal body portion may be configured to move between a first expanded configuration and a second collapsed configuration.

Alternatively or additionally to any of the examples above, in another example, wherein when at least one of the first or second implantable leadless pacing devices are positioned adjacent to the proximal body portion, the proximal body portion may be held in the expanded configuration.

Alternatively or additionally to any of the examples above, in another example, distal actuation of the first or second implantable leadless device may cause at least a portion of the proximal body portion to move from the expanded configuration to the collapsed configuration.

Alternatively or additionally to any of the examples above, in another example, the distal body portion may further comprise a reinforcing element.

Alternatively or additionally to any of the examples above, in another example, a proximal end of the second implantable leadless pacing device may be nested within a distal end region of the first implantable leadless pacing device.

Alternatively or additionally to any of the examples above, in another example, the second implantable leadless pacing device may have a smaller cross-sectional area than the first implantable leadless pacing device.

Alternatively or additionally to any of the examples above, in another example, the second implantable leadless pacing device may have a similar cross-sectional area to the first implantable leadless pacing device.

Alternatively or additionally to any of the examples above, in another example, the delivery device may further comprise an atraumatic element positioned on a proximal end of the second implantable leadless pacing device.

Alternatively or additionally to any of the examples above, in another example, the proximal body portion may have a length similar to a length of a more distal of the first or second implantable leadless pacing devices and the distal body portion may have a length similar to a length of a more proximal of the first or second implantable leadless pacing devices.

In another example, a delivery device for delivering two or more implantable leadless pacing devices may comprise an outer tubular member including a lumen extending from a proximal end to a distal end thereof, an intermediate tubular member including a lumen extending from a proximal end to a distal end thereof, the intermediate tubular member slidably disposed within the lumen of the outer tubular member, a distal holding section coupled to the intermediate tubular member and defining a cavity therein for receiving a proximal implantable leadless pacing device and a distal implantable leadless pacing device in a linear arrangement, the distal holding section having a proximal body portion comprising a first material and a distal body portion comprising a second material different from the first material, and an inner tubular member including a lumen extending from a proximal end to a distal end thereof, the inner tubular member slidably disposed within the lumen of the intermediate tubular member. The proximal body portion may be configured to move between a first expanded configuration and a second collapsed configuration.

Alternatively or additionally to any of the examples above, in another example, the first material may be more flexible than the second material.

Alternatively or additionally to any of the examples above, in another example, when at least one of the proximal or distal implantable leadless pacing devices are positioned adjacent to the proximal body portion, the proximal body portion may be held in the expanded configuration.

Alternatively or additionally to any of the examples above, in another example, distal actuation of the proximal or distal implantable leadless device may cause at least a portion of the proximal body portion to move from the expanded configuration to the collapsed configuration.

In another example, a method of delivering two implantable leadless pacing devices to two different chambers of a heart may comprise advancing a delivery device through the vasculature and into a first chamber of the heart. The delivery device may comprise a tubular member including a lumen extending from a proximal end to a distal end thereof, a distal holding section coupled to the tubular member and defining a cavity therein for receiving a proximal implantable leadless pacing device and a distal implantable leadless pacing device in a linear arrangement, the distal holding section having a proximal body portion and a distal body portion. The method may further comprise placing a distal tip of the distal holding section into contact with a target region of the first chamber of the heart, incrementally deploying the distal implantable leadless pacing device in the first chamber of the heart, after deploying the distal implantable leadless pacing device, distally advancing the tubular member into a second chamber of the heart placing a distal tip of the distal holding section into contact with a target region of the second chamber of the heart, and incrementally deploying the proximal implantable leadless pacing device in the second chamber of the heart.

Alternatively or additionally to any of the examples above, in another example, after deploying the distal implantable leadless pacing device, a length of the distal holding section having a diameter greater than a diameter of the tubular member may be shortened.

Alternatively or additionally to any of the examples above, in another example, incrementally deploying the distal implantable leadless pacing device may comprise applying a distal pushing force to a proximal end of the proximal implantable leadless pacing device.

Alternatively or additionally to any of the examples above, in another example, a distal end of the proximal implantable leadless pacing device may transfer a distal pushing force to a proximal end of the distal implantable leadless pacing device.

The above summary of some embodiments is not intended to describe each disclosed embodiment or every implementation of the present disclosure. The Figures, and Detailed Description, which follow, more particularly exemplify some of these embodiments.

BRIEF DESCRIPTION OF THE DRAWINGS

The disclosure may be more completely understood in consideration of the following detailed description in connection with the accompanying drawings, in which:

FIG. 8A is a cross-sectional view of another example implantable leadless pacing device;

FIG. 8B is a cross-sectional view of another example implantable leadless pacing device.

Figure 1:
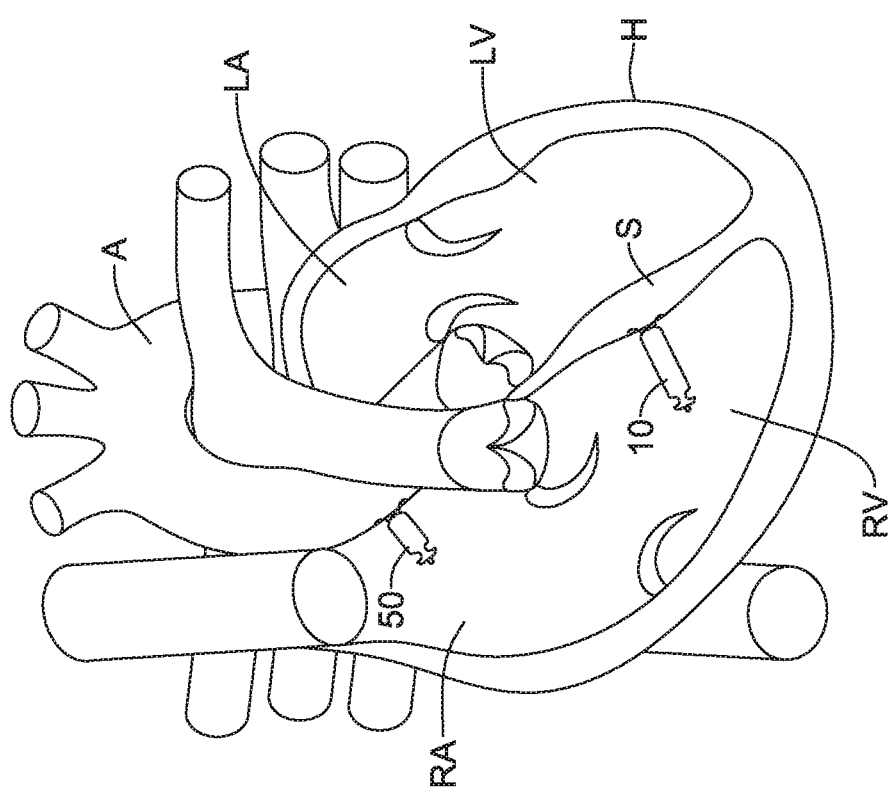
FIG. 1 is a plan view of example leadless pacing devices implanted within a heart.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure.

Cardiac pacemakers provide electrical stimulation to heart tissue to cause the heart to contract and thus pump blood through the vascular system. Conventional pacemakers typically include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. Leadless cardiac pacemakers are small capsules typically fixed to an intracardiac implant site in a cardiac chamber. The small capsule typically includes bipolar pacing/sensing electrodes, a power source (e.g., a battery), and associated electrical circuitry for controlling the pacing/sensing electrodes, and thus provide electrical stimulation to heart tissue and/or sense a physiological condition. The capsule may be delivered to the heart using a delivery device which may be advanced through a femoral vein, into the inferior vena cava, into the right atrium, through the tricuspid valve, and into the right ventricle. In some cases, it may be desirable to deliver a capsule to both the right ventricle and the right atrium (e.g. to provide a dual chamber pacing system). Dual chamber pacing is currently accomplished using transveous pacemakers. However, dual chamber leadless pacing may have many advantages including, but not limited to, the lack of a device pocket, fewer infections, ability to add leadless pacemakers in a modular fashion, etc. However delivering two leadless pacemakers with two separate delivery systems may be cost prohibitive as well as add procedure time. It may be further desirable to deliver both pacing devices using the same delivery system.

FIG. 1 illustrates a first example implantable leadless cardiac pacing device 10 (e.g., a leadless pacemaker) implanted in a chamber of a heart H, such as the right ventricle RV and a second example implantable leadless cardiac pacing device 50 (e.g., a leadless pacemaker) in another chamber of the H, such as the right atrium RA. In some cases, the device 10 may be affixed to the ventricular septum S, as shown. The left atrium LA, left ventricle LV, and aorta A are also illustrated. Although shown implanted in the right ventricle RV and right atrium RA, it is contemplated that the implantable device 10 may alternatively be implanted in any combination of the right ventricle RV, the right atrium RA, left atrium LA, left ventricle LV, or other cardiovascular location, if desired. In some instances, both devices 10, 50 may be implanted in the same chamber.

Figure 2:
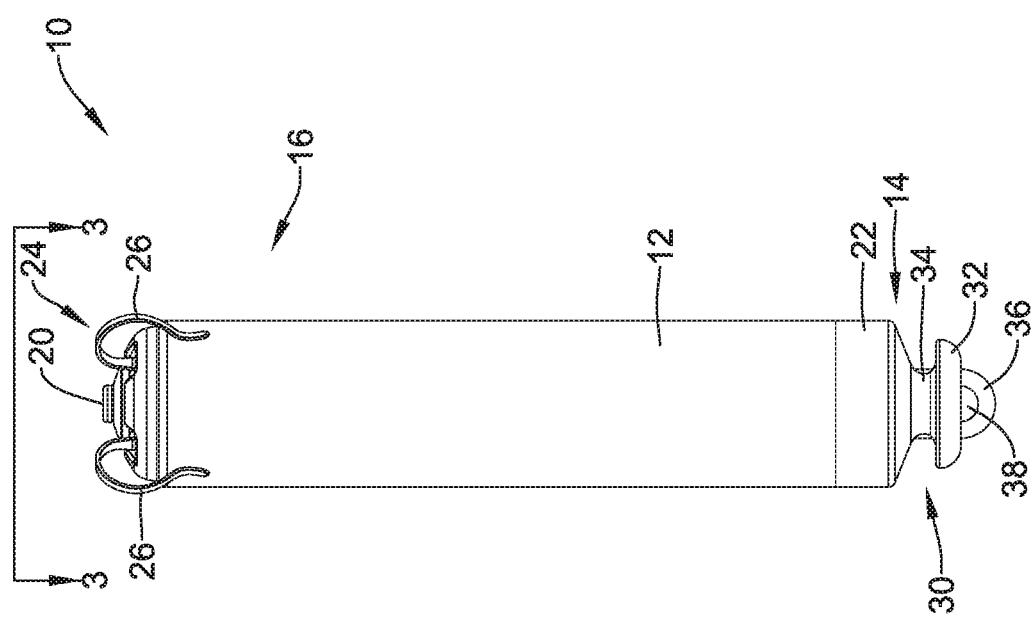
FIG. 2 is a side view of an example implantable leadless cardiac pacing device.
Figure 3:
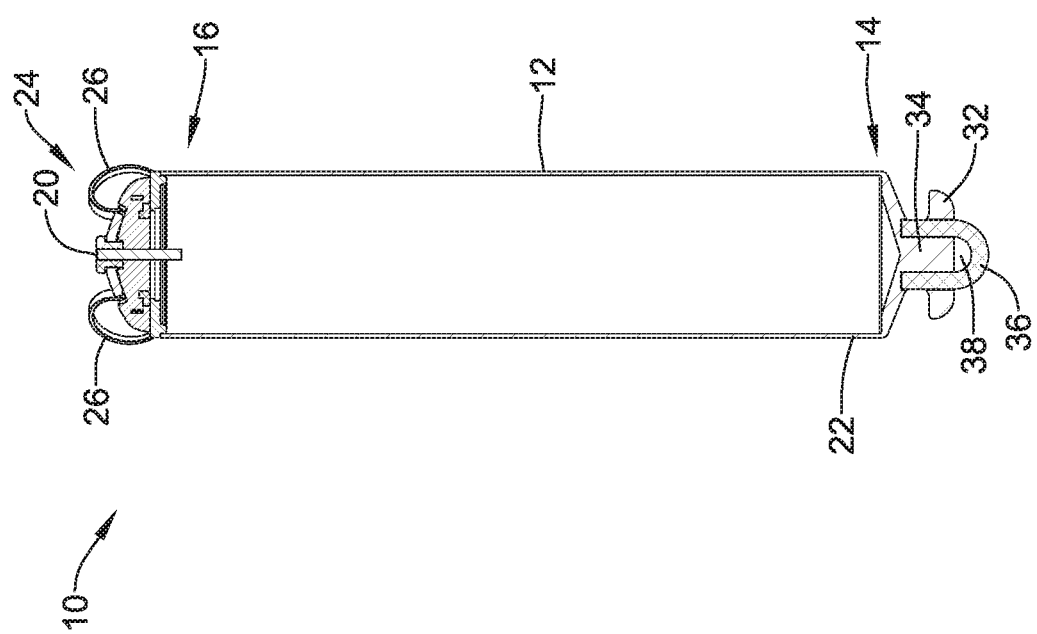
FIG. 3 is a cross-sectional view of the implantable leadless cardiac pacing device of FIG. 2.

A side view of the first illustrative implantable device 10 is shown in FIG. 2 and a cross-sectional view of the illustrative implantable device 10, taken at line 3-3 in FIG. 2, is illustrated in FIG. 3. The implantable device 10 may include a shell or housing 12 having a proximal end 14 and a distal end 16. The implantable device 10 may include a first electrode 20 positioned adjacent to the distal end 16 of the housing 12 and a second electrode 22 positioned adjacent to the proximal end 14 of the housing 12. For example, housing 12 may include a conductive material and may be insulated along a portion of its length. A section along the proximal end 14 may be free of insulation so as to define the second electrode 22. The electrodes 20, 22 may be sensing and/or pacing electrodes to provide electro-therapy and/or sensing capabilities. The first electrode 20 may be capable of being positioned against or may otherwise contact the cardiac tissue of the heart H while the second electrode 22 may be spaced away from the first electrode 20, and thus spaced away from the cardiac tissue.

The implantable device 10 may include a pulse generator (e.g., electrical circuitry) and a power source (e.g., a battery) within the housing 12 to provide electrical signals to the electrodes 20, 22 and thus control the pacing/sensing electrodes 20, 22. Electrical communication between the pulse generator and the electrodes 20, 22 may provide electrical stimulation to heart tissue and/or sense a physiological condition.

The implantable device 10 may include a fixation mechanism 24 proximate the distal end 16 of the housing 12 configured to attach the implantable device 10 to a tissue wall of the heart H, or otherwise anchor the implantable device 10 to the anatomy of the patient. As shown in FIG. 1, in some instances, the fixation mechanism 24 may include one or more, or a plurality of hooks or tines 26 anchored into the cardiac tissue of the heart H to attach the implantable device 10 to a tissue wall. In other instances, the fixation mechanism 24 may include one or more, or a plurality of passive tines, configured to entangle with trabeculae within the chamber of the heart H and/or a helical fixation anchor configured to be screwed into a tissue wall to anchor the implantable device 10 to the heart H. However, it is contemplated that the fixation mechanism 24 may be any structures configured to engage the heart tissue.

The implantable device 10 may include a docking member 30 proximate the proximal end 14 of the housing 12 configured to facilitate delivery and/or retrieval of the implantable device 10. For example, the docking member 30 may extend from the proximal end 14 of the housing 12 along a longitudinal axis of the housing 12. The docking member 30 may include a head portion 32 and a neck portion 34 extending between the housing 12 and the head portion 32. The head portion 32 may be an enlarged portion relative to the neck portion 34. For example, the head portion 32 may have a radial dimension from the longitudinal axis of the implantable device 10 which is greater than a radial dimension of the neck portion 34 from the longitudinal axis of the implantable device 10. The docking member 30 may further include a tether retention structure 36 extending from the head portion 32. The tether retention structure 36 may define an opening 38 configured to receive a tether or other anchoring mechanism therethrough. While the retention structure 36 is shown as having a generally "U-shaped" configuration, the retention structure 36 may take any shape which provides an enclosed perimeter surrounding the opening 38 such that a tether may be securably and releasably passed (e.g., looped) through the opening 38. The retention structure 36 may extend through the head portion 32, along the neck portion 34, and to or into the proximal end 14 of the housing 12, as is shown more clearly in FIG. 3. The docking member 30 may be configured to facilitate delivery of the implantable device 10 to the intracardiac site and/or retrieval of the implantable device 10 from the intracardiac site. Other docking members 30 are contemplated.

In some embodiments, the second illustrative implantable leadless cardiac pacing device 50 may be substantially identical in form and function the first implantable device 10. In other embodiments, the first implantable device 10 may be a larger device having more electrical complexity while the second implantable device 50 may be a smaller, satellite having simpler electronics, reduced functions, and/or smaller in physical size relative to the first device 10. The reverse configuration is also contemplated in which the second implantable device 50 may have more electrical complexity while the first implantable device 10 is a smaller, satellite having simpler electronics, reduced functions, and/or smaller in physical size relative the second device 50.

Figure 5:
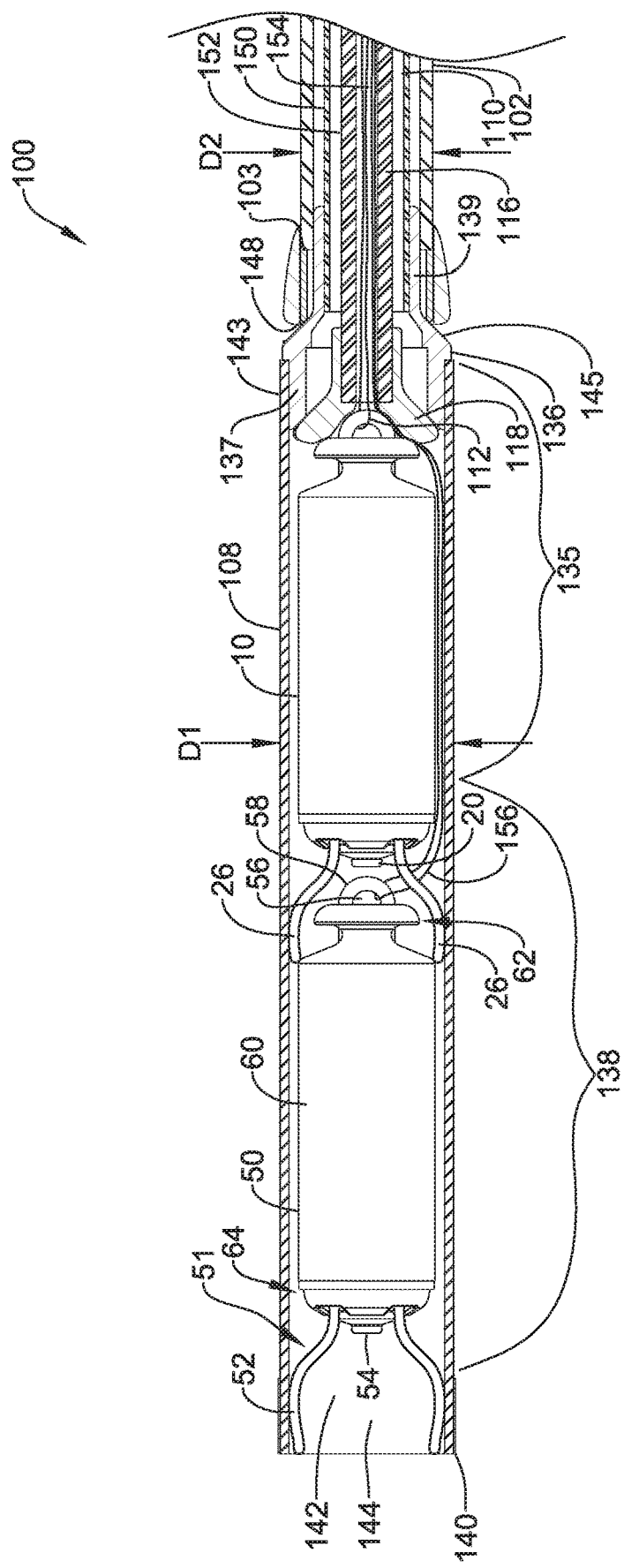
FIG. 5 is a partial cross-sectional side view of the distal portion of the delivery device of FIG. 4.

Referring briefly to FIG. 5, which illustrates a partial cross-sectional side view of the distal portion of an illustrative delivery device 100, the second implantable device 50 may be positioned distal to the first implantable device 10 within the delivery device 100. In some cases, the distal device 50 may have a smaller cross-sectional area such that the proximal end may "nest" within fixation mechanism 24 or distal end region of the proximal device 10. In other words, a proximal portion, e.g., the docking member 56, of the more distal second implantable device 50 may be located radially inward of the tines 26 or other fixation mechanism 24 of the more proximal first implantable device 10 such that the tines 26 of the proximal implantable device 10 surround the docking member 56 of the distal implantable device 50. Thus the distal ends of the tines 26 of the more proximal first implantable device 10 may extend distal of the proximal end (e.g., the docking member 56) of the more distal second implantable device 50 while positioned in the delivery confirmation within the delivery device 100. As will be discussed in more detail herein, the relative proximal and distal placement of the devices 10, 50 within the delivery device 100 may be determined by delivery order and is not intended to be limited to the orientation shown in the figures.

Still referring to FIG. 5, the second or distal device 50 may include a shell or housing 60 having a proximal end 62 and a distal end 64. The implantable device 50 may include a first electrode 54 positioned adjacent to the distal end 64 of the housing 60 and/or a second electrode (not explicitly shown) positioned adjacent to the proximal end 62 of the housing 60. For example, housing 60 may include a conductive material and may be insulated along a portion of its length. A section along the proximal end 62 may be free of insulation so as to define the second electrode. The electrodes 54 may be sensing and/or pacing electrodes to provide electro-therapy and/or sensing capabilities. The first electrode 54 may be capable of being positioned against or may otherwise contact the cardiac tissue of the heart H while the second electrode may be spaced away from the first electrode 54, and thus spaced away from the cardiac tissue.

The implantable device 50 may include a pulse generator (e.g., electrical circuitry) and a power source (e.g., a battery) within the housing 60 to provide electrical signals to the electrodes 54 and thus control the pacing/sensing electrodes 54. Electrical communication between the pulse generator and the electrodes 54 may provide electrical stimulation to heart tissue and/or sense a physiological condition. In some instances, the implantable device 50 may include an antenna-like extension for conducted communication to the first device 10, which may be positioned within the housing 60 if so provided.

The implantable device 50 may include a fixation mechanism 51 proximate the distal end 64 of the housing 60 configured to attach the implantable device 50 to a tissue wall of the heart H, or otherwise anchor the implantable device 50 to the anatomy of the patient. As shown in FIG. 5, in some instances, the fixation mechanism 51 may include one or more, or a plurality of hooks or tines 52 anchored into the cardiac tissue of the heart H to attach the implantable device 50 to a tissue wall. In other instances, the fixation mechanism 51 may include one or more, or a plurality of passive tines, configured to entangle with trabeculae within the chamber of the heart H and/or a helical fixation anchor configured to be screwed into a tissue wall to anchor the implantable device 50 to the heart H.

The implantable device 50 may include a docking member 58 proximate the proximal end 62 of the housing 60 configured to facilitate delivery and/or retrieval of the implantable device 50. The docking member 58 may be similar in form and function the docking member 30 of the first device 10. For example, the docking member 58 may extend from the proximal end 62 of the housing 60 along a longitudinal axis of the housing 60. The docking member 58 may include a tether retention structure defining an opening 56 configured to receive a tether or other anchoring mechanism therethrough. The docking member 58 may be configured to facilitate delivery of the implantable device 50 to the intracardiac site and/or retrieval of the implantable device 50 from the intracardiac site. Other docking members 58 are contemplated.

One aspect of the current disclosure relates to the delivery device and/or system used, for example, to deliver the devices 10, 50 to a suitable location within the anatomy (e.g., the heart). As may be appreciated, the delivery device may need to be navigated through relatively tortuous anatomy to deliver the devices 10, 50 to a suitable location. For instance, in some embodiments, the delivery devices 10, 50 may be advanced through the vasculature to a target region. In some example cases the devices 10, 50 may be advanced through a femoral vein, into the inferior vena cava, into the right atrium where the second device 50 is deployed, through the tricuspid valve, and into the right ventricle where the first device 10 is deployed. It may be desirable to provide the delivery system with certain features that may allow for delivery of two devices 10, 50 in a single delivery system.

Current delivery strategies may include delivering each device 10, 50 separately (e.g., using separate delivery systems) to the heart chamber. It may be desirable to provide a delivery system and delivery methods which allow both devices 10, 50 to be advanced simultaneously within the same delivery system and individually deployed at the target region for each device 10, 50 (e.g., the right ventricle for the first device 10 and the right atrium for the second device 50 or vice versa). Some illustrative delivery devices may be found in commonly assigned US Patent Publication No. 2016/0114156, titled DELIVERY DEVICES AND METHODS FOR LEADLESS CARDIAC DEVICES, US Patent Publication No. 2016/0114157, titled DELIVERY DEVICES AND METHODS FOR LEADLESS CARDIAC DEVICES, and U.S. patent application Ser. No. 15/354,432 filed on Nov. 17, 2016, titled DELIVERY DEVICES AND METHODS FOR LEADLESS CARDIAC DEVICES, the disclosures of which are incorporated herein by reference.

Figure 4:
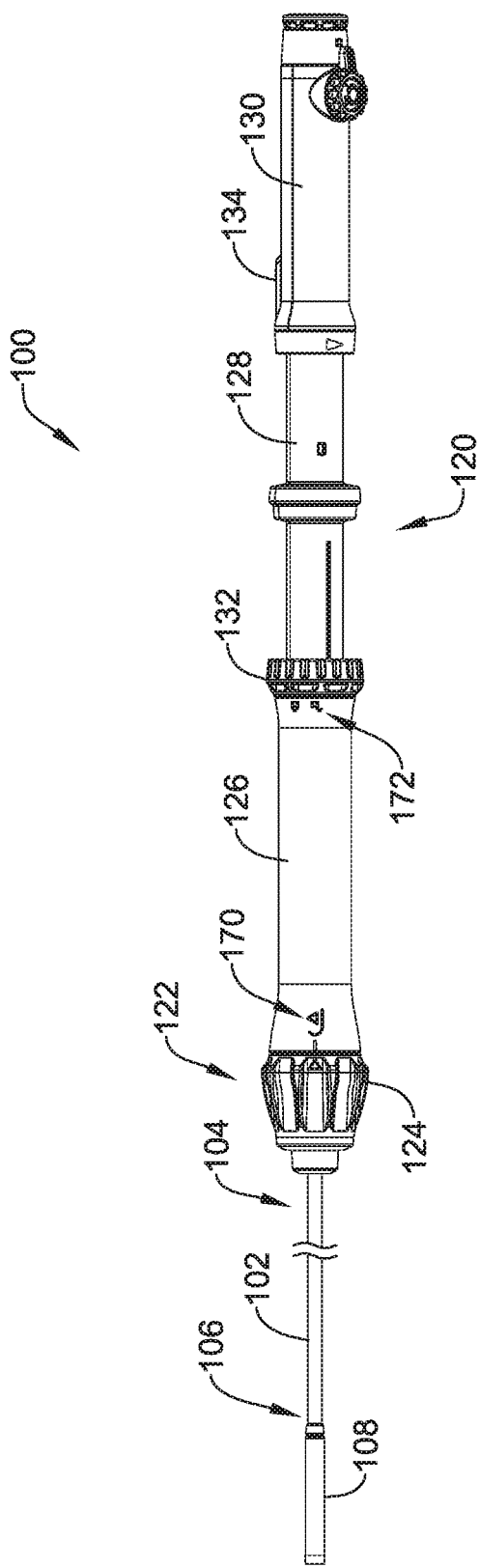
FIG. 4 is a plan view of an example delivery device for an implantable leadless cardiac pacing device.

FIG. 4 is a plan view of an illustrative delivery device 100, such as a catheter, that may be used to deliver the implantable devices 10, 50. The delivery device 100 may include an outer tubular member 102 having a proximal section 104 and a distal section 106. An intermediate tubular member 110 may be longitudinally slidably disposed within a lumen 150 of the outer tubular member 102 (see e.g., FIG. 5). An inner tubular member 116 may be longitudinally slidably disposed within a lumen 152 of the intermediate tubular member 110 (see e.g., FIG. 5). A distal holding section 108 may be attached to a distal end portion 114 of the intermediate tubular member 110. The delivery device 100 may also include a handle assembly 120 positioned adjacent to the proximal section 104 of the outer tubular member 102. In some embodiments, the outer tubular member 102 may include at least a section thereof that has an outer diameter D2 that is less than the outer diameter D1 of at least a portion of the holding section 108 (see e.g., FIG. 5).

The handle assembly 120 may include a first or distal hub portion 126 attached to, such as fixedly attached to, the proximal end section 104 of the outer tubular member 102, a second or intermediate hub portion 128 attached to, such as fixedly attached to, a proximal end section of the intermediate tubular member 110, and a third or proximal hub portion 130 attached to, such as fixedly attached to, a proximal end section of the inner tubular member 116 (see e.g., FIG. 5). The first hub portion 126, second hub portion 128, and third hub portion 130 may be positioned in a generally telescoping arrangement and longitudinally slidable relative to each other. Each of the first hub portion 126, the second hub portion 128, and the third hub portion 130 may be longitudinally slidable and rotatable relative to each other such that the outer tubular member 102, intermediate tubular member 110, and inner tubular member 116 may be individually actuated. In some instances, it may be desirable to move the outer tubular member 102, intermediate tubular member 110 and inner tubular member 116 simultaneously. The handle assembly 120 may include a multi-stage deployment mechanism or a first locking mechanism 134 to releasably couple the second hub portion 128 to the third hub portion 130 to prevent relative longitudinal movement therebetween, and thus prevent relative longitudinal movement between the intermediate tubular member 110 and the inner tubular member 116. The handle assembly 120 may also include a second locking mechanism 132 to releasably couple the first hub portion 126 to the second hub portion 128 to prevent relative longitudinal movement therebetween, and thus prevent relative longitudinal movement between the outer tubular member 102 and the intermediate tubular member 110.

The distal holding section 108 may be configured to receive both the first and second implantable devices 10, 50 therein. Thus, the entire length of both implantable devices 10, 50 may be contained within the distal holding section 108 during delivery to a cardiac site. For example, referring to FIG. 5, which illustrates a cross-sectional view of a distal portion of the delivery device 100, the holding section 108 may define a cavity 142 for slidably receiving the implantable devices 10, 50, and may include a distal opening 144 for slidable insertion and/or extraction of the implantable devices 10, 50 into and/or out of the cavity 142. It is further contemplated that the distal holding section 108 may be sized and shaped to accommodate more than two implantable devices each to be delivered sequentially, if so desired.

The distal holding section 108 may include a first or proximal body portion 135, a second or distal body portion 138, and a distal tip portion 140 that may be, for example, configured to be atraumatic to anatomy, such as a bumper tip. For example, as the catheter is navigated through the anatomy, the distal tip 140 may come into contact with anatomy. Additionally, when the catheter is used to deliver the device, the tip 140 of the delivery device 100 will likely come into contact with tissue adjacent the target site (e.g., cardiac tissue of the heart). A hard distal tip formed of the material of the outer tubular member 102 and/or intermediate tubular member 110 may injure a vessel wall or cardiac tissue. As such, it may be desirable to provide the delivery device 100 with a softer distal tip 140 that can be introduced into the anatomy and come into contact with anatomy adjacent the target cite without causing unnecessary trauma.

For example, the distal tip 140 may be made of a material that is softer than the second body portion 138, and in some cases, the first body portion 135 of the distal holding section 108. In some cases, the distal tip 140 may include a material that has a durometer that is less than the durometer of the material of the first and/or second body portions 135, 138. In some particular embodiments, the durometer of the material used in the distal tip 140 may be in the range of about 5 Shore D to about 70 Shore D, or for example, in the range of about 25 Shore D to about 65 Shore D. Additionally, the distal tip 140 may include a shape or structure that may make it less traumatic to tissue. For example, the distal tip 140 may have a distal surface, such as a tissue contacting surface, that is rounded or includes a curvature configured to be more atraumatic to tissue.

In some embodiments, all or a portion of the distal holding section 108 may include an inner surface that may be configured to resist getting caught on the fixation mechanisms 24, 51, such as the one or more, or a plurality of hooks or tines 26, 52 on the first and second device 10, 50. For example, all or a portion of the distal holding section 108 may include an inner layer or coating of harder or more lubricious material that resists force applied by the fixation mechanisms 24, 52 onto the inner surface of the distal holding section 108. For example, the distal holding section 108 may include a multi-layered structure, and an inner layer may be made of a material that is harder than an outer layer.

The devices 10, 50 may be loaded one after the other (e.g., in a linear arrangement) into the distal holding section 108 such that the devices 10, 50 may be individually and sequentially deployed. For example, it may be desirable to deliver the second device 50 to the right atrium prior to delivering the first device 10 to the right ventricle. In such an instance, the first device 10 may be loaded proximal to the second device 50. In other words, at least during initial loading of the device 10, 50, the first device 10 may be generally adjacent to the first body portion 135 in a more proximal location and the second device 50 may be generally adjacent to the second body portion 138 in a more distal location. This is just an example. The reverse configuration is also contemplated. For example, when using a jugular or cephalic approach, it may be desired to place a device in the right ventricle prior to placing a device in the right atrium.

The inner tubular member 116 may be disposed (e.g., slidably disposed) within a lumen 152 of the intermediate tubular member 110. The inner tubular member 116 may be engaged by a user near or at the third hub portion 130, and extend through a lumen 152 of the intermediate tubular member 110 and into the distal holding section 108. A distal portion 118 of the inner tubular member 116 may be capable of engaging the device 10, and the inner tubular member 116 may be used to "push" the device 10 in a distal direction. The proximal device 10 may transfer this distal force to the distal device 50 which is pushed distally out from distal holding section 108 so as to deploy and anchor the distal device 50 within a target region (e.g., a region of the heart such as the right atrium). For example, the electrode 20 of the proximal device 10 may contact the docking member 58 of the distal device 50 as the first device 10 is distally advanced. In some cases, the docking member 58 of the distal device 50 may include features configured to protect the electrode of the proximal device 10 from damage during deployment of the second device 50.

For example, referring briefly to FIGS. 8A and 8B which illustrate a cross-section view of the second device 50 having atraumatic features, the docking member 58 may include an atraumatic element such as, but not limited to, a silicone bumper, dissolvable or bioabsorbable bumper or ring (e.g., sugar, mannitol), or the like. In one illustrative embodiment, the docking member 58 may be partially or fully coated in an atraumatic layer 70, as shown in FIG. 8A, to form a protective bumper. The atraumatic layer 70 may be formed from silicone, a bioabsorbable material, or other soft material, as desired. In some instances, the atraumatic layer 70 may disposed on an outward facing surface 72 (e.g., facing away from the opening 56). This arrangement may protect the electrode 20 of the proximal device 10 while allowing a retention feature to pass through the opening 58. In some embodiments, the atraumatic layer 70 may be disposed over only a portion of the outward facing surface 72. For example, the atraumatic layer 70 may be disposed on a proximal-most portion of the outer facing surface 72 of the docking member 58.

In another illustrative embodiment, the docking member 58 may have a ring 80 positioned about the outward facing surface 72 thereof. It is contemplated that the ring 80 may include an aperture 82 sized and shaped to receive the electrode 20 of the proximal device 10 therein. The area of the device 10 surrounding the electrode 20 may contact the proximal end 84 of the ring 80 to push the distal device 50 from the distal holding section 108. This may allow the distal device 50 to be distally advanced without the electrode 20 of the proximal device contacting the distal device 10. It is contemplated that the ring 80 may be formed from a material configured to be atraumatic such as, but not limited to, silicone, a bioabsorbable material, or other soft material. However, it is contemplated that other materials may be used. For example, the ring 80 may be formed from the same material as the docking member 58. In some cases, the ring 80 may be formed as a unitary structure with the docking member 58 while in other cases, the ring 80 may be formed separately and attached to the docking member 58 using techniques known in the art.

A tether 156 or other retaining feature may be used to releasably secure the implantable device 50 to the delivery device 100. In some instances, the tether 156 may be a single or unitary length of material that may extend from a proximal end (not explicitly shown) of a lumen 154 of the inner tubular member 116, out through the distal portion 118, through the opening 56 of the docking member 58 and return to the proximal end of the inner tubular member 116 through the lumen 154 such that both ends of the tether 156 are positioned adjacent to the third hub portion 130. In some instances, the ends of the tether 156 may be secured within a locking feature in the third hub portion 130, although this is not required. While the tether 156 is shown with both ends extending along one side of the proximal device 10, it is contemplated that one end may extending along a first side of the proximal device 10 and the other end may extend along a different radial location (e.g., radially offset from the first end). In some cases, the second end of the tether 156 may be about 180° from, or generally opposite to the, the first end. This is just an example.

Figure 6:
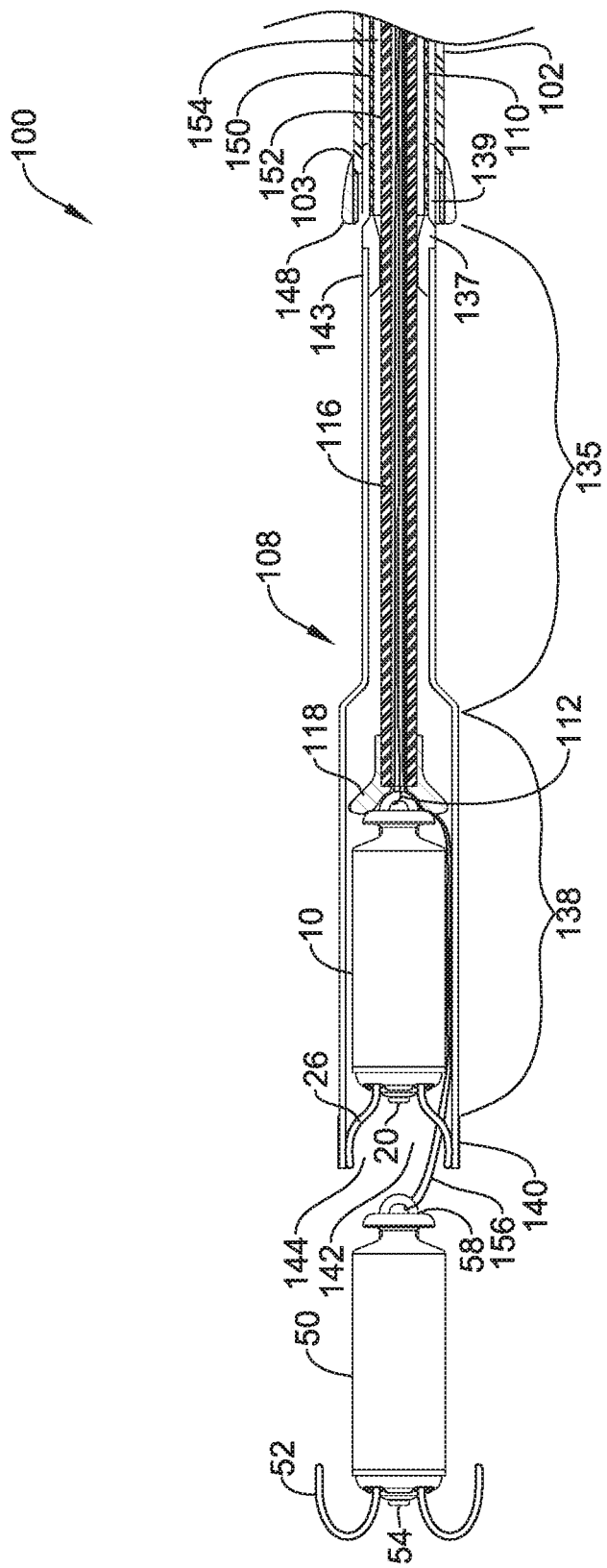
FIG. 6 is a partial cross-sectional side view of the distal portion of the delivery device of FIG. 4 in a partially deployed configuration.

FIG. 6 illustrates a partial cross-sectional view of the illustrative delivery system with the distal implantable device 50 deployed from the distal holding section 108. While the distal device 50 is not shown actively engaging a tissue, it should be understood the distal device 50 may be deployed into a tissue (e.g., the right atrium) such that the electrode 54 is brought into contact with said tissue. The first body portion 135 of the distal holding section 108 may be made from a soft, flexible, or stretchable material, such that as the devices 10, 50 are distally advanced, the first body portion 135 is configured to radially collapse, as shown in FIG. 6 such that a length of the distal holding section having a diameter greater than the outer tubular member 102 is shortened or reduced when only a single device (e.g., proximal device 10) is in the distal holding section 108. For example, the first or proximal body portion 135 may be held in an expanded configuration by the proximal device 10 when positioned in the cavity of the proximal body portion 135. In other words, the proximal device 10 may bias the proximal body portion 135 in a radially expanded or stretched state with the circumferential surface of the proximal device 10 engaged against an inner surface of the proximal body portion 135. As the proximal device 10 is distally advanced, the first body portion 135 may reduce in diameter as the biasing force of the proximal device 10 is removed. In some cases, in the absence of the device 10, the first body portion 135 may revert to or have a size and shape similar to the intermediate tubular member 110, or otherwise be reduced in outer diameter. In other cases, in the absence of the device 10, the first body portion 135 may revert to or conform to an outer surface of the inner tubular member 116, or otherwise be reduced in outer diameter. Reducing the diameter of the proximal body portion 135 may allow the distal holding section 108 to have the shortest possible length when delivering the second, proximal device 10 to the right ventricle. For example, a shorter rigid section may allow the clinician to more easily manipulate the delivery system 100 through the tricuspid valve from the inferior vena cava, as will be discussed in more detail herein. In some instances, the outer tubular member 102 may be extended over the radially collapsed first body portion 135 after deployment of the distal device 50, but prior to advancing the delivery system 100 through the tricuspid valve and/or deployment of the proximal device 10.

It is contemplated that the first body portion 135 and the second body portion 138 may be formed from differing materials to achieve the desired rigidity (e.g., to maintain the fixation elements 26, 52 in an elongated configuration) and the desired flexibility (e.g., to allow the first body portion 135 to radially reduce in diameter) of the two regions. However, the body portions 135, 138 may be formed from the same material. In some cases, the second body portion 138 may include a reinforcing element (e.g., helically wound filament, an embedded mesh, etc.) Some illustrative delivery devices having a reinforcing element in the distal holding section may be found in commonly assigned US Patent Publication No. 2016/0114156, titled DELIVERY DEVICES AND METHODS FOR LEADLESS CARDIAC DEVICES, the disclosure of which is incorporated herein by reference. In some cases, the second (e.g., more rigid) body portion 138 may have a length similar to the overall length of the device that is deployed last. It is contemplated that the second body portion 138 may have a length sufficient to maintain the fixation elements 26, 52 of both devices 10, 50 in an elongated configuration during delivery and up to device 10, 50 deployment.

Other structures or material combinations which reduce the length of the more rigid portion of the distal holding section 108 are also contemplated. For example, in some cases, the first body portion 135 may include a plurality of longitudinally collapsing bellows. These bellows may be configured to collapse (e.g., shorten in a longitudinal direction) in an accordion like manner as the distal device 50 is deployed.

In other embodiments, the first body portion 135 may telescope relative to the second body portion 138 to reduce the length of the distal holding section 108 upon deployment of the distal implantable device 50. For example, the first body portion 135 may be configured to longitudinally telescope into the second body portion 138 to reduce the overall length of the distal holding section 108, or the second body portion 138 may be configured to longitudinally telescope into the first body portion 135 to reduce the overall length of the distal holding section 108.

Figure 7:
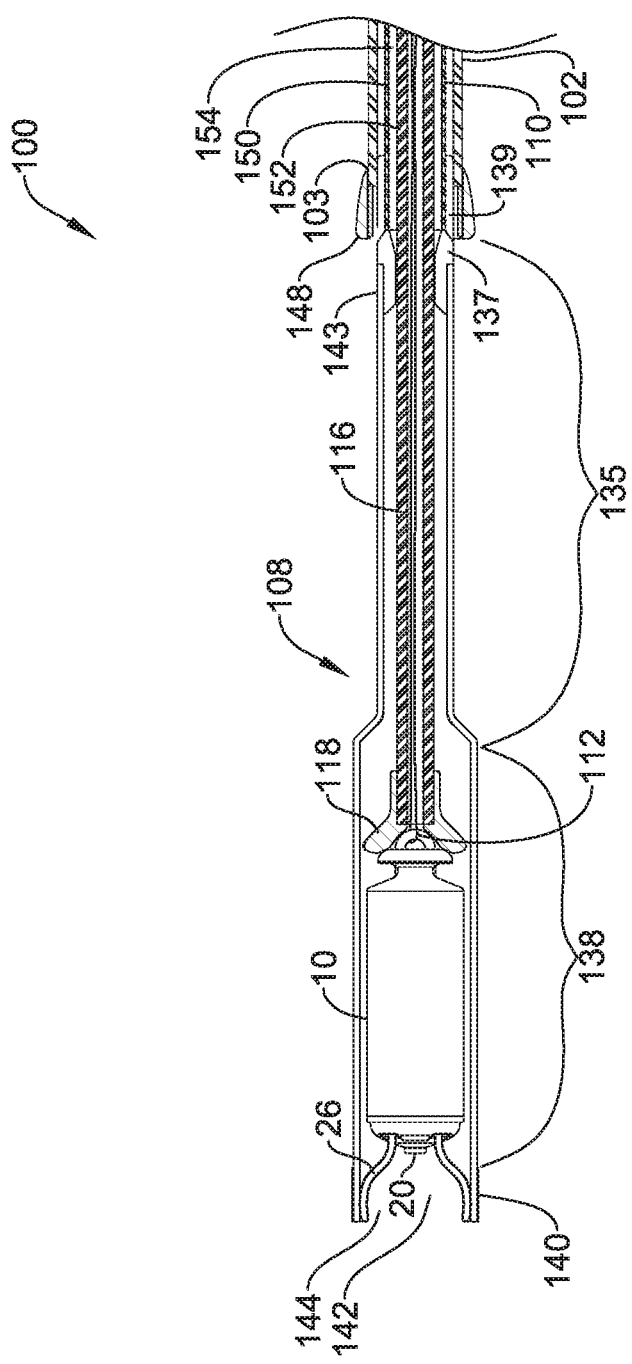
FIG. 7 is a partial cross-sectional side view of the distal portion of the delivery device of FIG. 4 with one of the leadless pacing devices deployed.

Once the distal device 50 has been deployed and its placement verified, the tether 156 may be removed, and the delivery device 100 prepared to deliver the proximal device 10 to a second location, as shown in FIG. 7. The delivery device 100 may be manipulated into position and the proximal device 10 deployed in a manner similar to the distal device 50. For example, the inner tubular member 116 may be engaged by a user near or at the third hub portion 130, and extend through a lumen 152 of the intermediate tubular member 110 and into the distal holding section 108. A distal portion 118 of the inner tubular member 116 may be capable of engaging the device 10, and the inner tubular member 116 may be used to "push" the device 10 out from distal holding section 108 so as to deploy and anchor device 10 within a target region (e.g., a region of the heart such as the right ventricle).

The inner tubular member 116 may have a lumen 154 extending from the proximal end (not explicitly shown) to a distal portion 118 thereof. A tether 112 or other retaining feature may be used to releasably secure the proximal device 10 to the delivery device 100. In some instances, the tether 112 may be a single or unitary length of material that may extend from a proximal end of the lumen 154, out through the distal portion 118, through the opening 38 of the proximal device 10 and return to the proximal end of the inner tubular member 116 through the lumen 154 such that both ends of the tether 112 are positioned adjacent to the third hub portion 130. In some instances, the ends of the tether 112 may be secured within a locking feature in the third hub portion 130, although this is not required.

In order to more specifically place or steer the delivery device 100 to a position adjacent to the intended target, the delivery device 100 may be configured to be deflectable or articulable or steerable. Referring to FIG. 4, for example, the outer tubular member 102 and/or intermediate tubular member 110 may include one or more articulation or deflection mechanism(s) that may allow for the delivery device 100, or portions thereof, to be deflected, articulated, steered and/or controlled in a desired manner. For example, the outer tubular member 102 may include at least a portion thereof that can be selectively bent and/or deflected in a desired or predetermined direction. This may, for example, allow a user to orient the delivery device 100 such that the holding section 108 is in a desirable position or orientation for navigation or delivery of the device 10 to a target location. The outer tubular member 102 may be deflected, for example, along a deflection region.

A wide variety of deflection mechanisms may be used. In some example embodiments, deflection may be effected by one or more actuation members, such as pull wire(s) extending between a distal portion of the outer tubular member 102 and an actuation mechanism 122 near the proximal end of the outer tubular member 102. As such, the one or more pull wires may extend both proximally and distally of the desired deflection or bending region or point. This allows a user to actuate (e.g., "pull") one or more of the pull wires to apply a compression and/or deflection force to at least a portion of the outer tubular member 102 and thereby deflect or bend the outer tubular member 102 in a desired manner. In addition, in some cases the one or more wires may be stiff enough so that they can also be used to provide a pushing and/or tensioning force on the outer tubular member 102, for example, to "push" or "straighten" the shaft into a desired position or orientation.

In some embodiments, the actuation member takes the form of a continuous wire that is looped through or otherwise coupled to a distal end region of the outer tubular member 102 so as to define a pair of wire sections. Other embodiments are contemplated, however, including embodiments where the actuation member includes one or a plurality of individual wires that are attached, for example, to a metal or metal alloy ring adjacent the distal end region of the outer tubular member 102.

The actuation mechanism 122 may include a mechanism that may allow for applying tension (i.e. pulling force), or compression (i.e. pushing force), or both, on the actuation member(s). In some embodiments, the actuation mechanism 122 may include an external rotatable member 124 connected to and rotatable about the longitudinal axis of the handle assembly 120. The rotatable member 124 may threadingly engage an internal member that is attached to the proximal end of the actuation member(s) or pull wires. When the external rotatable member 124 is rotated in a first rotational direction, the internal member translates in a first longitudinal direction, thereby applying tension to the pull wire(s), which applies compression force to the shaft, so as to deflect the outer tubular member 102 from an initial position to a deflected position. When the external rotatable member 124 is rotated in a second rotational direction, the internal member translates in a second longitudinal direction, thereby reducing and/or releasing the tension on the pull wire(s), and allowing the outer tubular member 102 to relax back toward the initial position. Additionally, in some cases, as mentioned above, where the one or more wires may be stiff enough, rotation of the rotatable member 124 in the second rotational direction such that the internal member translates in a second longitudinal direction may apply compression to the wire(s), such that the wire(s) may apply tension to the outer tubular member 102 and "push" the outer tubular member 102 back toward an initial position, and possibly into additional positions beyond the initial position.

The one or more articulation and/or deflection mechanism (s) may also entail the outer tubular member 102 including structure and/or material that may provide for the desired degree and/or location of the deflection when the compressive or tensile forces are applied. For example, the outer tubular member 102 may include one or more sections that include structure and/or material configured to allow the shaft to bend and/or deflect in a certain way when a certain predetermined compressive and/or tensile force is applied. For example, the shaft may include one or more sections that are more flexible than other sections, thereby defining a bending or articulating region or location. Some such regions may include a number of varying or changing flexibility characteristics that may define certain bending shapes when predetermined forces are applied. Such characteristics may be achieved through the selection of materials or structure for different sections of the outer tubular member 102.

In other embodiments, other articulation and/or deflection mechanism(s) are contemplated. For example, all or a portion of the delivery device 100, such as the outer tubular member 102, may be made of a shape memory material, such as a shape memory polymer and/or a shape memory metal. Such materials, when stimulated by an actuation mechanism, such as a change in temperature or the application of an electrical current, may change or move from a first shape to a second shape. As such, these material(s) and mechanism(s) may be used to deflect or bend the outer tubular member 102 in a desired manner. Other suitable deflection mechanism(s) that are able to deflect the delivery device 100 may also be used. Such alternative mechanisms may be applied to all other embodiments shown and/or discussed herein, and others, as appropriate.

Furthermore, the outer tubular member 102 may include one or more predefined or fixed curved portion(s) along the length thereof. In some cases, such curved sections may be configured to fit with particular anatomies or be configured for better navigation or delivery of the devices 10, 50. Additionally, or alternatively, some such curved sections may be configured to allow the outer tubular member 102 to be predisposed to be bent and/or deflected in a certain direction or configuration when compression and/or tension forces are applied thereto. It is contemplated that the outer tubular member 102 may be a laser cut metallic tubing, a braid reinforced polymeric tubing, or other flexible tubular structure as desired.

Returning again to FIG. 5, the distal holding section 108 may be affixed to a distal end portion 114 of the intermediate tubular member 110. The distal holding section 108 may include a hub portion 136 and a tubular body portion 138. In some instances, the hub portion 136 may be formed from a metal or metal alloy while the body portion 138 may be formed from a polymeric material, although this is not required. In some instances, a proximal region 143 of the body portion 138 may be heat bonded to a distal end portion 137 of the hub portion 136, or otherwise affixed. The hub portion 136 may include a tapered intermediate region 145 disposed between a proximal end portion 139 and the distal end portion 137.

In some embodiments, the outer tubular member 102 may include a metal ring or tip adjacent the distal end 103 thereof for attaching one or more pull wires thereto. It is contemplated that the outer tubular member 102 may further include a lubricious liner, such as, but not limited to a polytetrafluoroethylene (PTFE) liner. The proximal end portion 139 of the hub portion 136 may extend proximally into the lumen 150 of the outer tubular member 102. In some instances, an outer surface of the proximal end portion 139 may form an interference fit with an inner surface of the outer tubular member 102. It is contemplated that the outer surface of the proximal end portion 139 and the inner surface of the outer tubular member 102 may be coupled in a tapered engagement. For example, the distal end 103 of the outer tubular member 102 may flare radially outwards in the distal direction and/or the proximal end portion 139 may taper radially inward in the proximal direction. The two angled surface may engage as the proximal end portion 139 is proximally retracted within the outer tubular member 102. Other coupling arrangements may be used as desired.

It is contemplated that as the outer tubular member 102 is bent to navigate the implantable device 10 to the desired location, the proximal end portion 139 may advance distally and disengage from the inner surface of the outer tubular member 102 creating a kink point or weakened region adjacent to the bonding region. Proximally retracting the intermediate tubular member 110 to bring the intermediate region 145 into contact with the outer tubular member 102 at contact point 148 and/or bringing the proximal end portion 139 into the outer tubular member 102 and fixing the intermediate tubular member 110 in this configuration may help prevent migration of the distal holding section 108 during navigation of the delivery device 100 to the desired location. Such a configuration may also place the intermediate tubular member 110 in tension while the distal holding section 108 applies a compression force on the outer tubular member 102, as will be discussed in more detail below. As discussed above, a locking mechanism 132 in the handle assembly 120 may be utilized to releasably maintain the outer tubular member 102 and the intermediate tubular member 110 in a desired orientation.

Figure 9A:
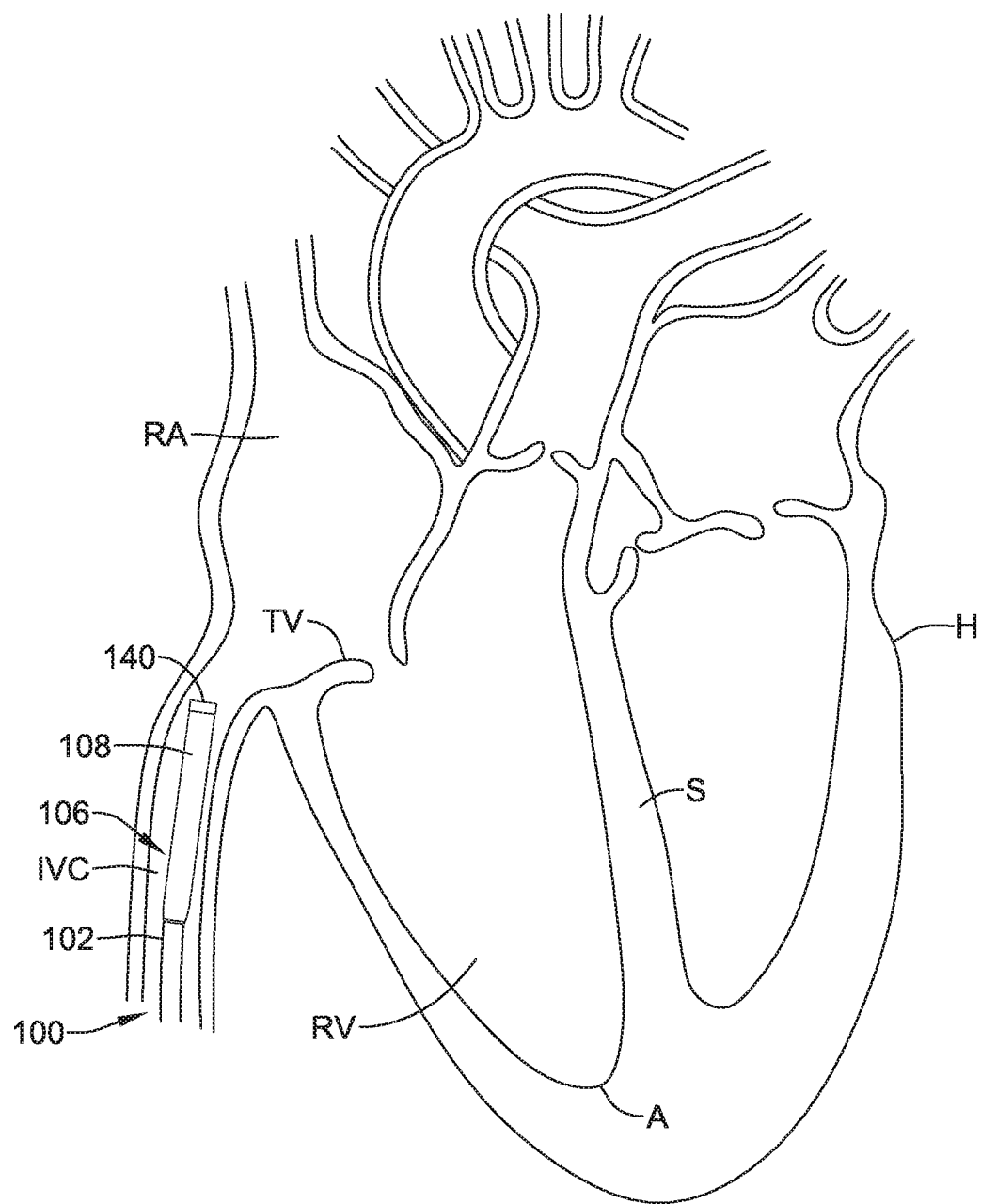
FIGS. 9A-9G are schematic views illustrating the use of the illustrative delivery device to deploy two implantable leadless cardiac pacing devices.

Referring now to FIGS. 9A-9G, an exemplary method for deploying two implantable devices 10, 50 to the tissue of the heart using a single delivery device 100 will now be described with respect to the distal section and distal holding section 108. The delivery device 100 may be introduced into the vasculature through the femoral vein through a previously introduced sheath catheter (not explicitly shown). The delivery device 100 may be introduced through any desired location and with or without the use of an introducer sheath as desired. The delivery device 100 may be advanced through the vasculature to the desired treatment location, which, in the case of a leadless cardiac pacing device, may be a chamber of the heart H. For example, the delivery device 100 may be advanced through the vasculature to the inferior vena cava IVC, as shown in FIG. 9A, and into the right atrium RA. The clinician may use the actuation mechanism 122 to deflect the distal end portion 106 of the outer tubular member 102 in a desired manner to facilitate advancement and/or placement of the delivery device 100. During advancement of the delivery device 100, the handle assembly 120 may be in a fully extended configuration. In such a configuration, the third hub portion 130 may be at its proximal-most location relative to the second hub portion 128 and the first hub portion 126 may be at its distal-most location relative to the second hub portion 128. When the handle assembly 120 is in its fully extended configuration, the inner tubular member 116, intermediate tubular member 110, and the outer tubular member 102 may be oriented in the manner illustrated in FIG. 5. The delivery device 100 can be imaged using known techniques to ensure accurate placement of the devices 10, 50.

Figure 9B:
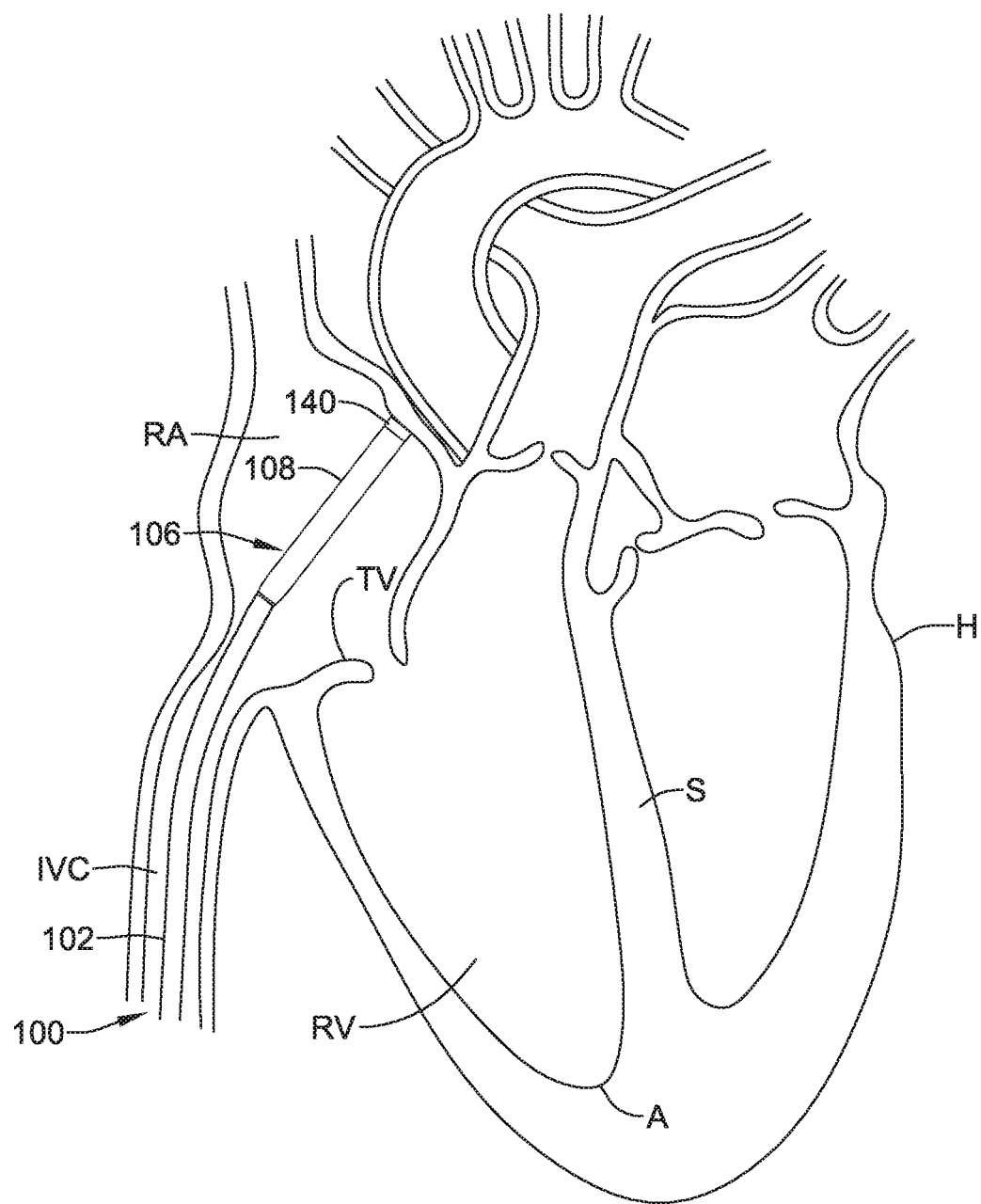

The distal tip portion 140 of the distal holding section 108 may be brought into contact with the desired placement location of the right atrium RA, as shown in FIG. 9B. In some cases, the outer tubular member 102 may remain in the interior vena cava IVC and the intermediate tubular member 110 extended or telescoped to achieve the desired positioning of the distal tip portion 140, although this is not required. In some instances, the location of the distal tip portion 140 may be confirmed with contrast media and imaging. For example, contrast confirmation may be used to confirm the distal tip portion 140 is engaged with a wall of the heart H prior to deploying the distal implantable device 50. It is further contemplated that the intermediate tubular member 110 may be formed from a flexible material, such as, but not limited to a 35 D durometer polyether block amide (PEBA, for example available under the trade name PEBAX®). It is contemplated that a flexible material may buckle or flex with an applied force (e.g. from the clinician) when the distal tip portion 140 is in contact with the wall of the heart H. This may provide additional confirmation under imaging that the distal tip portion 140 is engaged with the wall of the heart H. It is further contemplated that a flexible intermediate tubular member 110 may facilitate navigation of the delivery device 100.

Once the distal tip portion 140 of the distal holding section 108 has been positioned adjacent to the cardiac tissue where the device 50 is desired, deployment of the distal device 50 can begin. It is contemplated that the location of the distal tip portion 140 may be confirmed with contrast media and imaging, as described above. The first stage of the deployment of the distal device 50 may enable activation of the fixation mechanism 51. The device 50 may be distally advanced out of the distal holding section 108 to deploy the hooks or tines 52 from the distal holding section 108 to engage the hooks or tines 52 in the heart tissue while the proximal portion of the device 50 remains within the distal holding section 108. In some embodiments, the location and/or fixation of the device 50 may be confirmed with contrast media, although this is not required. The fixation and placement of the distal device 50 in the right atrium may be verified. For example, a "tug" test on the tether 156 may be used to determine if the hooks or tines 52 are secured within the tissue. Various electrical measurements may be used to check placement and contact of electrode 54. If necessary, the tether 156 may be used to pull the distal device 50 back into the distal holding section 108, if necessary, to reposition the distal device 50. Care may be taken when using the proximal device 10 to push the distal device 50 out of the distal holding section to prevent deployment of the fixation mechanism 24 of the proximal device 10. For example, the distal device 50 may be only partially pushed out of the distal holding section 108 using the inner tubular member 110. For example, the distal device 50 may be distally advanced until the fixation mechanism 51 engages the tissue. However, this is not required.

Figure 9C:
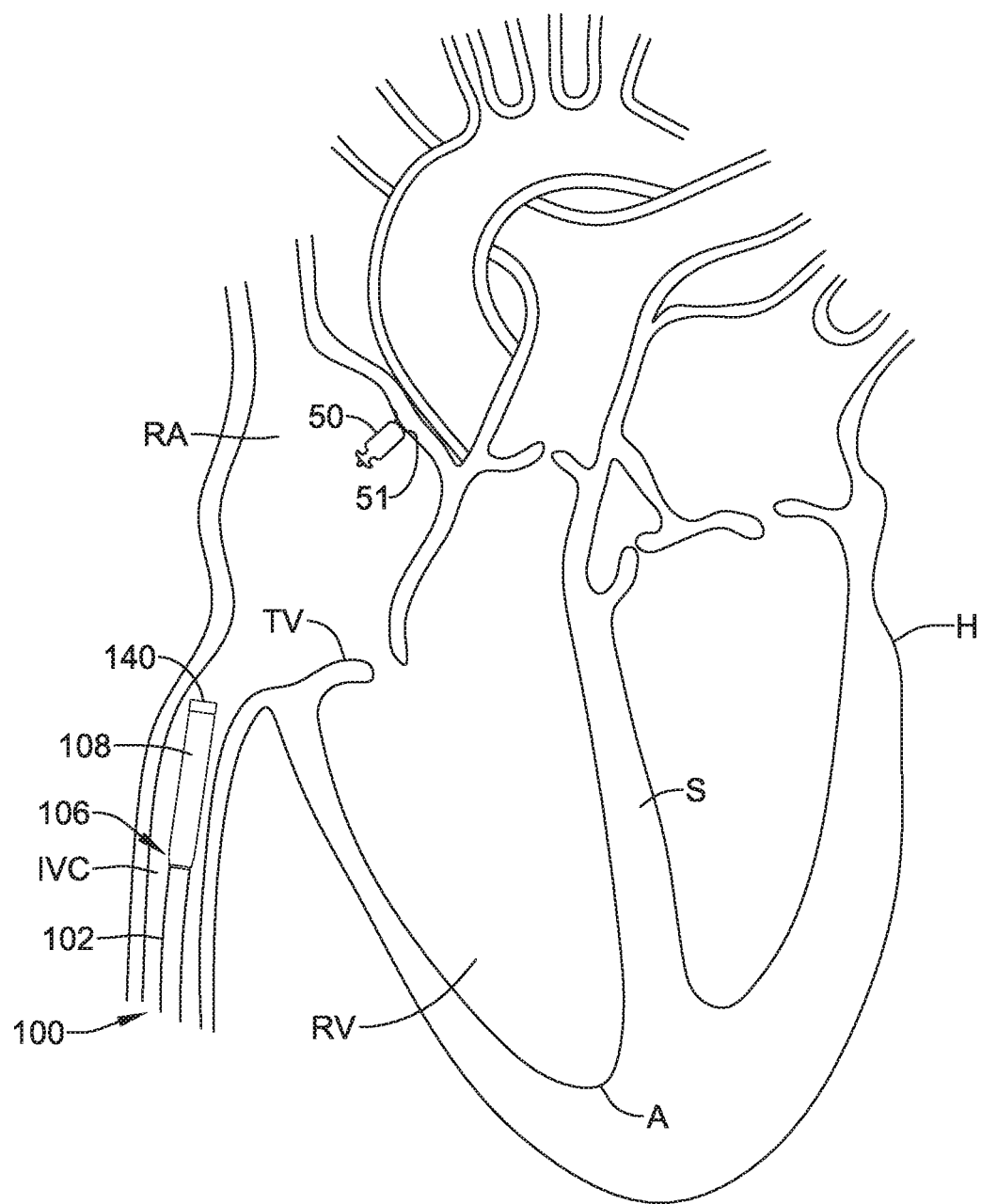

Once fixation and placement of the distal device 50 have been verified, the second stage of the deployment of the device 50 may proximally retract the distal holding section 108, and thus the intermediate tubular member 110, relative to the inner tubular member 116 to fully deploy the device 50, as shown in FIG. 9C. Once the distal device 50 has been deployed, the first body portion 135 may radially collapse (e.g., reduce in diameter) such that a length of the distal holding section have a diameter greater than the outer tubular member 102 is shortened. Once the clinician has determined that the position of the device 50 is satisfactory and the fixation mechanism 51 is securely engaged with the heart tissue, the intermediate tubular member 110, including the distal holding section 108, of the delivery device 100 can be proximally retracted towards or into the inferior vena cava IVC. The distal holding section 108 may again be advanced into the right atrium RA.

Figure 9D:
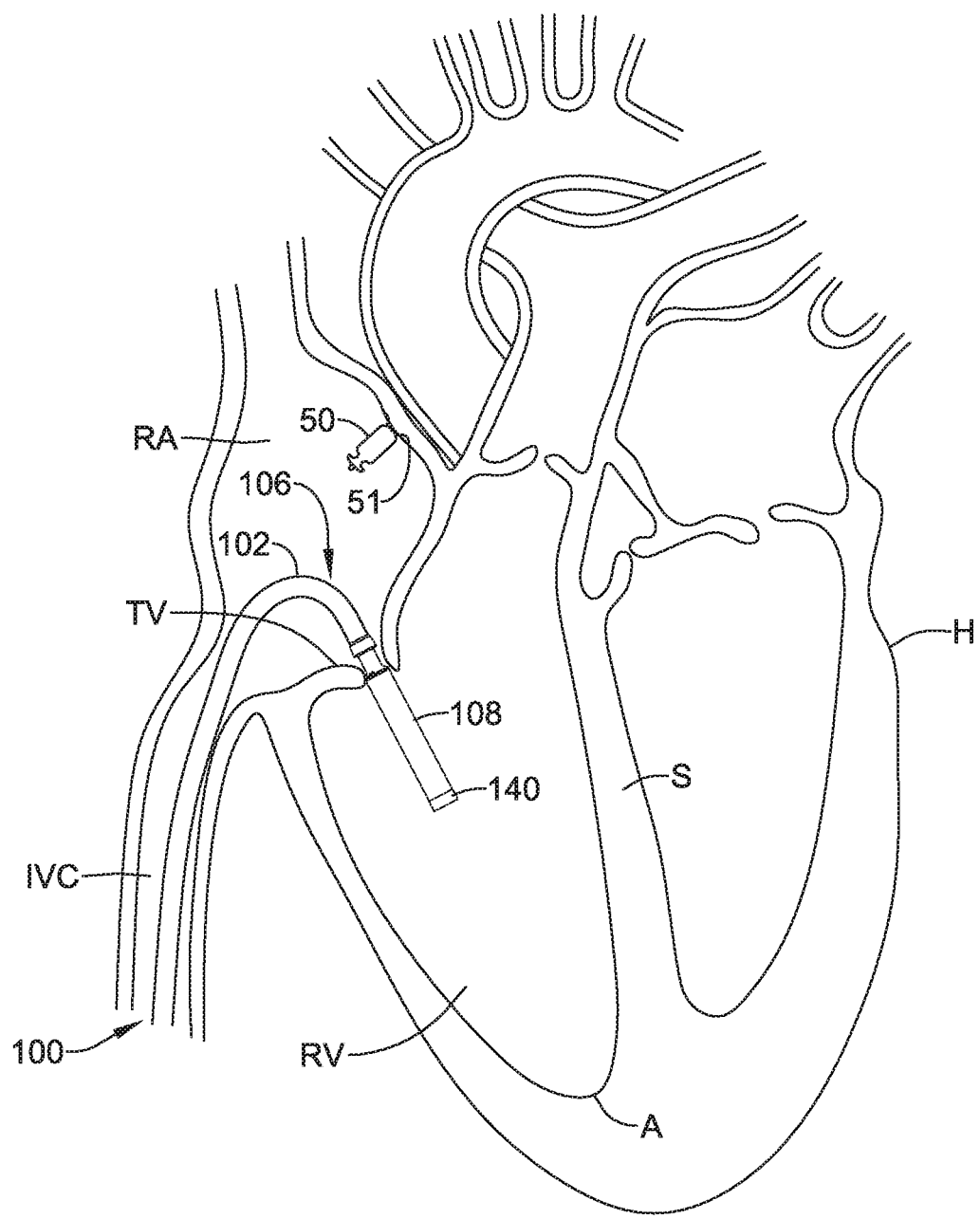

As the distal tip portion 140 of the distal holding section 108 enters the junction of the inferior vena cava IVC and the right atrium RA, the clinician may begin to deflect the outer tubular member 102 (and/or intermediate tubular member 110), as described above with respect to FIG. 4. It is contemplated that the outer tubular member 102 may be capable of deflection angles of up 180°, or more. The clinician may use a combination of skillful catheter manipulation (e.g. sweeping, rotating, etc.) and deflection to locate the tricuspid valve TV. Once the tricuspid valve TV has been located, the clinician may further advance and/or deflect the delivery device 100 to advance the distal holding section 108 into the right ventricle RV, as shown in FIG. 9D. In some instances, deflection of the outer tubular member 102 may be sufficient to move the distal tip portion 140 across the tricuspid valve TV and into the right ventricle RV. In other instances, the outer tubular member 102 may first be deflected and then the delivery device 100 pushed across the tricuspid valve TV.

Once the distal holding section 108 has been advanced across the tricuspid valve TV and into the right ventricle RV, the clinician may advance the distal holding section 108 and the intermediate tubular member 110 without advancing the outer tubular member 102 (i.e., telescoping the intermediate tubular member 110). It is contemplated that the entire distal holding section 108 need not be in the right ventricle RV to begin advancing the distal holding section 108 and the intermediate tubular member 110 without advancing the outer tubular member 102. For example, in some instances only a portion of the length of the distal holding section 108 may be in the right ventricle RV prior to telescoping the distal holding section 108 from the outer tubular member 102. It is contemplated that, in some instances, less than one-third or less than one-half of the distal holding section 108 may be positioned in the right ventricle RV when the intermediate tubular member 110 is telescoped distal of the distal end of the outer tubular member 102. In other instances, the entire length or substantially the entire length of the distal holding section 108 may be positioned in the right ventricle RV when the intermediate tubular member 110 is telescoped distal of the distal end of the outer tubular member 102. An average heart may have an average distance of approximately 7.5 centimeters between the tricuspid valve TV and an apex A of the right ventricle RV. In some instances, the distance between the tricuspid valve TV and the apex A of the right ventricle RV may be in the range of 4 to 12 centimeters or in the range of 6 to 10 centimeters. In a smaller heart, it may be possible for a portion of the distal holding section 108 to remain in the right atrium RA while in a larger heart the distal holding section 108 may need to be fully advanced into the right ventricle RV. For example, the distal holding portion 108 may have a length in the range of 3.5 to 5.5 centimeters or in the range of 4.0 to 5.0 centimeters. In some instances, the delivery device 100 may have a telescoping distance in the range of 3 to 10 centimeters or the in the range of 4 to 7 centimeters, for example. The length of the distal holding section 108 in combination with the telescoping feature of the delivery device 100 may be sufficient to bring the distal tip portion 140 into contact with the apex A of the right ventricle RV without fully advancing the distal holding section 108 into the right ventricle RV (e.g. prior to telescoping the intermediate tubular member 110). However, in some cases, the proximal device 10 may be delivered to the ventricular septum. Some illustrative delivery devices and method for delivering a device to the ventricular septum may be found in commonly assigned U.S. Patent Application No. 62/478, 897, titled DELIVERY DEVICES AND METHODS FOR LEADLESS CARDIAC DEVICES, filed on Mar. 30, 2017, the disclosure of which is incorporated herein by reference.

Figure 9E:
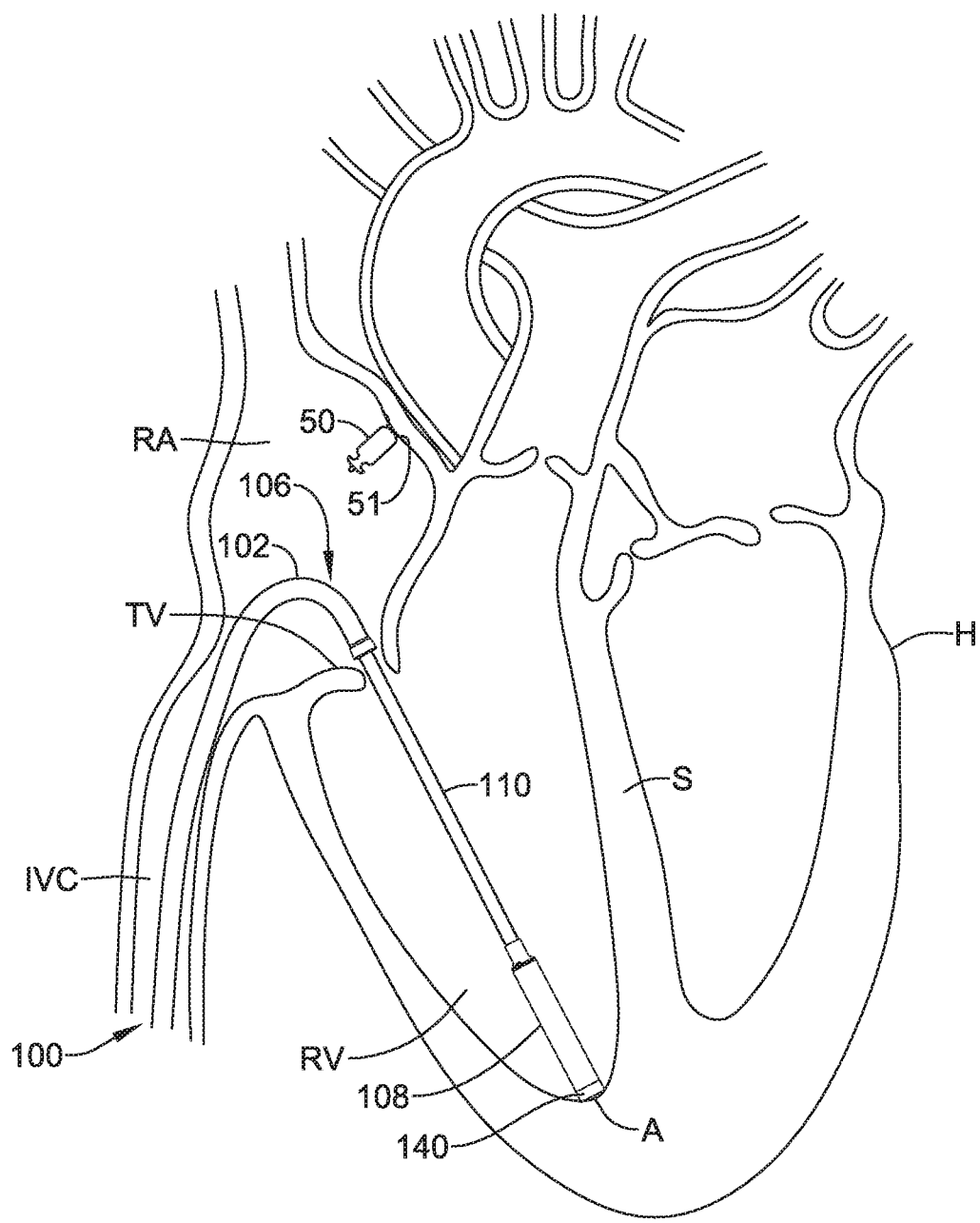

The distal holding section 108 and the intermediate tubular member 110 may be advanced until the distal tip portion 140 of the distal holding section 108 contacts the wall of the heart H, as shown in FIG. 9E. In some instances, the distal tip portion 140 may be placed in contact with the apex A of the right ventricle RV. In some instances, the location of the distal tip portion 140 may be confirmed with contrast media and imaging. For example, contrast confirmation may be used to confirm the distal tip portion 140 is engaged with a wall of the hearth H prior to deploying the proximal implantable device 10. It is further contemplated that the intermediate tubular member 110 may be formed from a flexible material, such as, but not limited to a 35 D durometer polyether block amide (PEBA, for example available under the trade name PEBAX®). It is contemplated that a flexible material may buckle or flex with an applied force (e.g. from the clinician) when the distal tip portion 140 is in contact with the wall of the heart H. This may provide additional confirmation under imaging that the distal tip portion 140 is engaged with the wall of the heart H. It is further contemplated that a flexible intermediate tubular member 110 may facilitate navigation of the delivery device 100.

Figure 9F:
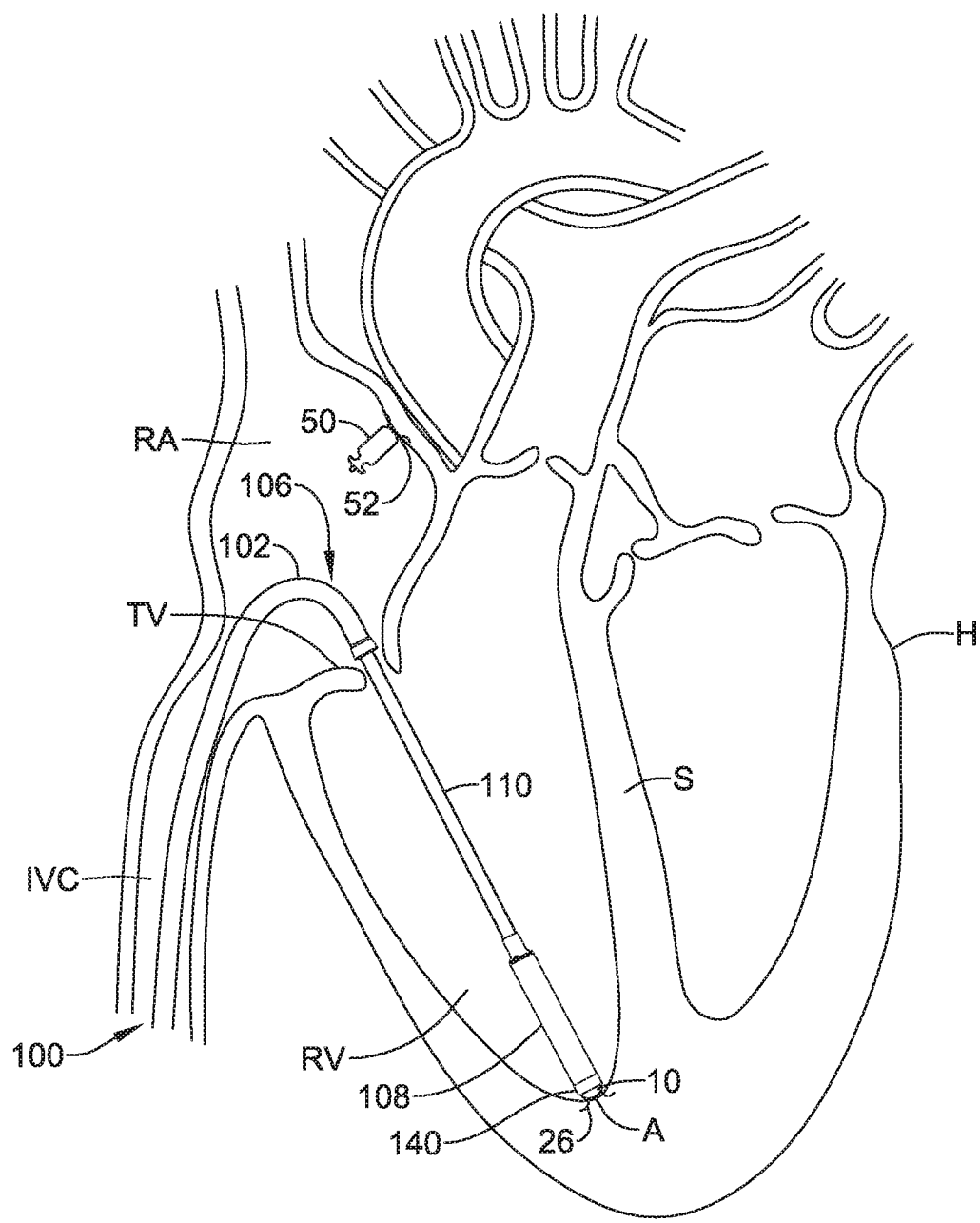
Figure 9G:
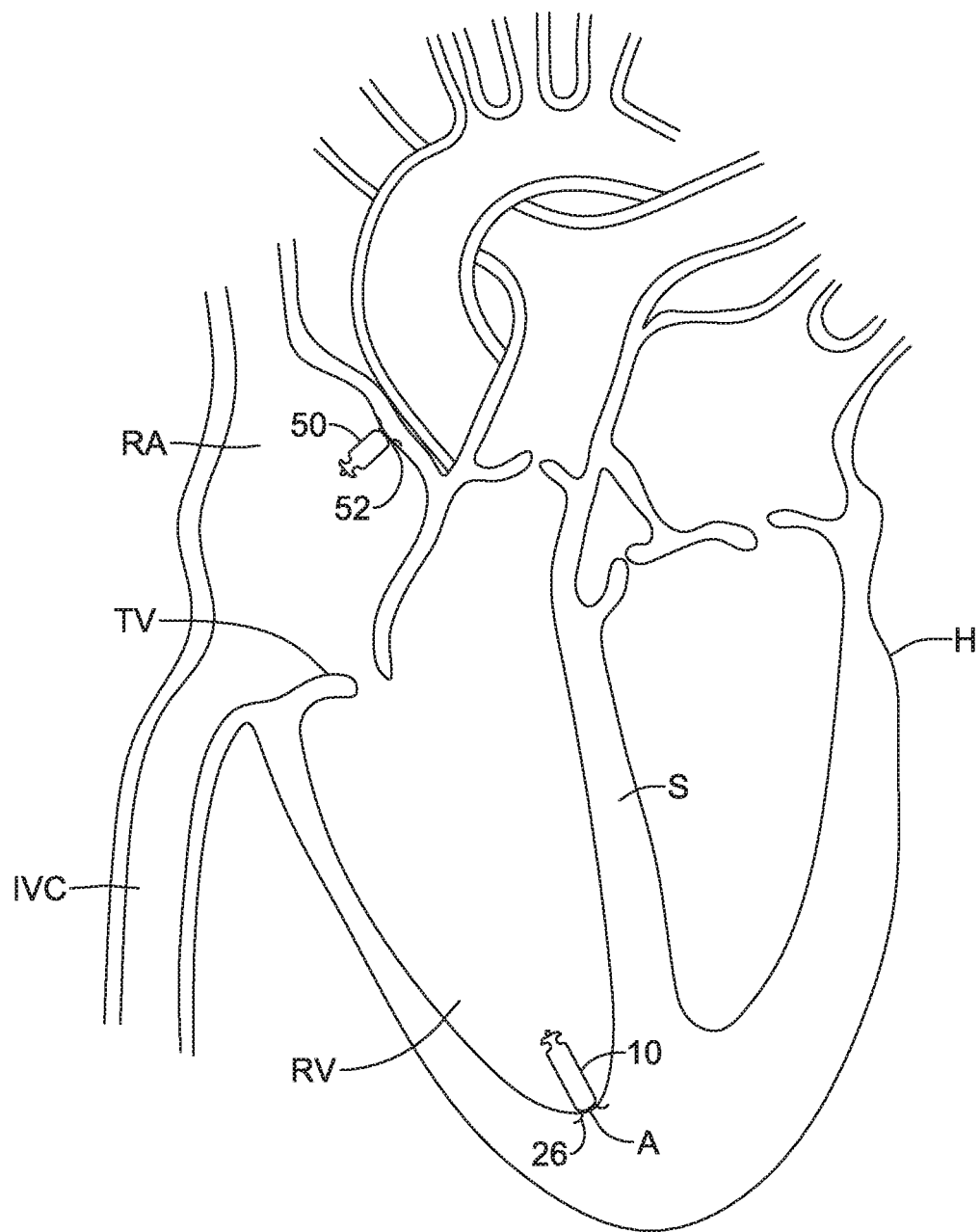

Once the distal tip portion 140 of the distal holding section 108 has been positioned adjacent to the cardiac tissue where the device 10 is desired, deployment of the device 10 can begin. The first stage of the deployment of the proximal device 10 may enable activation of the fixation mechanism 24. The proximal device 10 may be distally advanced out of the distal holding section 108 to deploy the hooks or tines 26 from the distal holding section 108 to engage the hooks or tines 26 in the heart tissue while the proximal portion of the device 10 remains within the distal holding section 108, as shown in FIG. 9F. In some embodiments, the location and/or fixation of the device 10 may be confirmed with contrast media, although this is not required. The second stage of the deployment of the device 10 may proximally retract the distal holding section 108, and thus the intermediate tubular member 110, relative to the inner tubular member 116 to fully deploy the device 10. Once the clinician has determined that the position of the device 10 is satisfactory and the fixation mechanism 24 is securely engaged with the heart tissue, the intermediate tubular member 110, including the distal holding section 108, of the delivery device 100 can be proximally retracted, as shown in FIG. 9G.

While a method has been described in which the devices 10, 50 are delivered to the right atrium and right ventricle, it is contemplated that a similar method may be used to deliver the devices 10, 50 to other chambers or a single chamber of the heart, as desired. It is contemplated that using a single delivery device, such as the delivery device 100 described herein, to deliver two separate leadless cardiac pacemakers (and in some cases to two separate chambers) may reduce implant time, number of passes of catheters, and/or system cost of a dual device leadless system.

The materials that can be used for the various components of the delivery devices, such as delivery device 100 (and/or other delivery structures disclosed herein) and the various members disclosed herein may include those commonly associated with medical devices. For simplicity purposes, the following discussion makes reference the delivery device 100, and components of thereof. However, this is not intended to limit the devices and methods described herein, as the discussion may be applied to other similar delivery systems and/or components of delivery systems or devices disclosed herein.

The delivery device 100 and/or other components of delivery system may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the polymer can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the delivery device 100 and/or other components of delivery system may be doped with, made of, or otherwise include a radiopaque material. Radiopaque materials are understood to be materials capable of producing a relatively bright image on a fluoroscopy screen or another imaging technique during a medical procedure. This relatively bright image aids the user of the delivery device 100 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the delivery device 100 to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A delivery device for delivering two or more implantable leadless pacing devices, the delivery device comprising:
   a tubular member including a lumen extending from a proximal end to a distal end thereof;
   a distal holding section located at the distal end of the tubular member and defining a cavity therein, the distal holding section having a proximal body portion and a distal body portion located distal of the proximal body portion, wherein an entirety of the distal body portion is more rigid than the proximal body portion; and
   a first implantable leadless pacing device positioned within the proximal body portion and a second implantable leadless pacing device positioned within the distal body portion in a linear arrangement, wherein the first and second implantable leadless pacing devices are not attached to each other.

2. The delivery device of claim 1, wherein the distal end of the tubular member includes an atraumatic tip made of a material that is softer than the distal body portion.

3. The delivery device of claim 1, wherein the proximal body portion and the distal body portion comprise different materials.

4. The delivery device of claim 1, wherein the proximal body portion is configured to move between a first expanded configuration and a second collapsed configuration.

5. The delivery device of claim 4, wherein when at least one of the first or second implantable leadless pacing devices are positioned adjacent to the proximal body portion, the proximal body portion is held in the expanded configuration.

6. The delivery device of claim 5, wherein distal actuation of the first or second implantable leadless device causes at least a portion of the proximal body portion to move from the expanded configuration to the collapsed configuration.

7. The delivery device of claim 1, wherein the distal body portion further comprises a reinforcing element.

8. The delivery device of claim 1, wherein a proximal end of the second implantable leadless pacing device is nested within a distal end region of the first implantable leadless pacing device.

9. The delivery device of claim 1, wherein the second implantable leadless pacing device has a smaller cross-sectional area than the first implantable leadless pacing device.

10. The delivery device of claim 1, wherein the second implantable leadless pacing device has a similar cross-sectional area to the first implantable leadless pacing device.

11. The delivery device of claim 1, further comprising an atraumatic element positioned on a proximal end of the second implantable leadless pacing device.

12. The delivery device of claim 2, wherein the proximal body portion comprises a first material and the distal body portion comprises a second material, wherein the first material is more flexible than the second material.

13. A delivery device for delivering two or more implantable leadless pacing devices, the delivery device comprising:
   a tubular member including a lumen extending from a proximal end to a distal end thereof;
   a distal holding section located at the distal end of the tubular member and defining a cavity therein, the distal holding section having a proximal body portion and a distal body portion located distal of the proximal body portion;
   a first implantable leadless pacing device positioned within the proximal body portion of the distal holding section, the first implantable leadless pacing device having a proximal end and a distal end, the distal end having a plurality of fixation elements; and
   a second implantable leadless pacing device positioned within the distal body portion of the distal holding section, the second implantable leadless pacing device having a proximal end and a distal end, the distal end having a plurality of fixation elements;
   wherein the proximal end of the second implantable leadless pacing device is located proximal of a distal-most extent of the plurality of fixation elements of the first implantable pacing device such that the proximal end of the second implantable leadless pacing device is surrounded by the plurality of fixation elements on the first implantable leadless pacing device;
   wherein the distal body portion is more rigid than the proximal body portion and only the proximal body portion is configured to move between a first radially expanded configuration and a second radially collapsed configuration.

14. The delivery device of claim 13, wherein the plurality of fixation elements on the first and second implantable leadless pacing devices include tines movable between an elongated configuration and an anchoring configuration, wherein the more rigid distal body portion has a length extending over the tines on both the first and second implantable leadless pacing devices.

15. The delivery device of claim 13, wherein the proximal end of the first implantable leadless pacing device includes a first docking member and the proximal end of the second implantable leadless pacing device includes a second docking member, wherein a first tether is releasably secured to the first docking member and extends proximally therefrom, wherein a second tether is releasably secured to the second docking member and extends proximally therefrom, wherein the first and second tethers are separate elements.

16. The delivery device of claim 13, wherein the first and second implantable leadless pacing devices are not attached to each other.

17. A delivery device for delivering two or more implantable leadless pacing devices, the delivery device comprising:
a tubular member including a lumen extending from a proximal end to a distal end thereof;
a distal holding section located at the distal end of the tubular member and defining a cavity therein, the distal holding section having a proximal body portion and a distal body portion located distal of the proximal body portion;
a first implantable leadless pacing device and a second implantable leadless pacing device positioned within the distal holding section in a linear arrangement with the first implantable leadless pacing device positioned proximal of the second implantable leadless pacing device within the distal holding section, wherein a proximal end of the first implantable leadless pacing device includes a first docking member and a proximal end of the second implantable leadless pacing device includes a second docking member, wherein the second docking member is configured to contact an electrode on a distal end of the first implantable leadless pacing device as the first device is advanced distally during delivery;
a first tether releasably secured to the first docking member and extending proximally therefrom;
a second tether releasably secured to the second docking member and extending proximally therefrom;
wherein the first and second tethers are separate elements.

18. The delivery device of claim 17, wherein the proximal end of the second implantable leadless pacing device is surrounded by a plurality of fixation elements on the first implantable leadless pacing device with the proximal end of the second implantable leadless pacing device located proximal of a distalmost extent of the plurality of fixation elements of the first implantable pacing device, wherein the first and second implantable leadless pacing devices are not attached to each other.

19. The delivery device of claim 17, wherein the distal body portion is more rigid than the proximal body portion.

20. The delivery device of claim 17, wherein at least a portion of a proximal facing surface of the second docking member includes a separate atraumatic layer.

\* \* \* \* \*